US010993807B2

(12) United States Patent
Duffy et al.

(10) Patent No.: US 10,993,807 B2
(45) Date of Patent: May 4, 2021

(54) SYSTEMS AND METHODS FOR PERCUTANEOUSLY SUPPORTING AND MANIPULATING A SEPTAL WALL

(71) Applicant: Medtronic Vascular, Inc., Santa Rosa, CA (US)

(72) Inventors: Niall Duffy, Galway (IE); Jeffrey Sandstrom, Scandia, MN (US); James R. Keogh, Maplewood, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 229 days.

(21) Appl. No.: 16/191,228

(22) Filed: Nov. 14, 2018

(65) Prior Publication Data

US 2019/0142587 A1    May 16, 2019

Related U.S. Application Data

(60) Provisional application No. 62/586,993, filed on Nov. 16, 2017.

(51) Int. Cl.
*A61F 2/24*    (2006.01)
*A61B 17/00*    (2006.01)
(Continued)

(52) U.S. Cl.
CPC ........ *A61F 2/2433* (2013.01); *A61B 17/0057* (2013.01); *A61B 17/0401* (2013.01);
(Continued)

(58) Field of Classification Search
None
See application file for complete search history.

(56) References Cited

U.S. PATENT DOCUMENTS

| 3,874,338 A | 4/1975 | Happel |
| 4,836,204 A | 6/1989 | Landymore et al. |

(Continued)

FOREIGN PATENT DOCUMENTS

| FR | 2714284 A1 | 6/1995 |
| WO | 9918871 A1 | 4/1999 |

(Continued)

OTHER PUBLICATIONS

International Search Report and Written Opinion dated Jul. 29, 2019 in PCT/US2018/061360.

*Primary Examiner* — Shaun L David

(57) ABSTRACT

A catheter-based system for percutaneously supporting and articulating a septal wall of a heart includes a catheter and a flanged device. The flanged device includes a distal anchor and a proximal anchor, and has a radially collapsed configuration and a radially expanded configuration. When the flanged device is in the radially expanded configuration and disposed through a transseptal puncture in the septal wall, the flanged device is configured to anchor to the septal wall to permit manipulation thereof whereby an angle between an axis through the transseptal puncture and an axis through a native valve is reduced. The proximal anchor and the distal anchor may each be self-expanding or balloon expandable. The flanged device may further include a flanged device shaft. The flanged device shaft may be releasably coupled to the catheter.

6 Claims, 36 Drawing Sheets

(51) Int. Cl.
*A61B 17/04* (2006.01)
*A61B 17/34* (2006.01)

(52) U.S. Cl.
CPC ........ *A61B 17/3423* (2013.01); *A61F 2/2427* (2013.01); *A61F 2/2436* (2013.01); *A61B 2017/00243* (2013.01); *A61B 2017/00575* (2013.01); *A61B 2017/00606* (2013.01); *A61B 2017/00867* (2013.01); *A61B 2017/048* (2013.01); *A61B 2017/3425* (2013.01); *A61F 2/2454* (2013.01)

(56) References Cited

U.S. PATENT DOCUMENTS

| | | | |
|---|---|---|---|
| 5,284,488 | A | 2/1994 | Sideris |
| 5,334,217 | A | 8/1994 | Das |
| 5,425,744 | A | 6/1995 | Fagan et al. |
| 5,433,727 | A | 7/1995 | Sideris |
| 5,451,235 | A | 9/1995 | Lock et al. |
| 5,486,193 | A | 1/1996 | Bourne et al. |
| 5,507,811 | A | 4/1996 | Koike et al. |
| 5,527,338 | A | 6/1996 | Purdy |
| 5,634,936 | A | 6/1997 | Linden et al. |
| 5,649,950 | A | 7/1997 | Bourne et al. |
| 5,702,421 | A | 12/1997 | Schneidt |
| 5,709,707 | A | 1/1998 | Lock et al. |
| 5,725,552 | A | 3/1998 | Kotula et al. |
| 5,741,297 | A | 4/1998 | Simon |
| 5,797,960 | A | 8/1998 | Stevens et al. |
| 5,846,261 | A | 12/1998 | Kotula et al. |
| 5,853,422 | A | 12/1998 | Huebsch et al. |
| 5,861,003 | A | 1/1999 | Latson et al. |
| 5,904,703 | A | 5/1999 | Gilson |
| 5,928,250 | A | 7/1999 | Koike et al. |
| 5,944,738 | A | 8/1999 | Amplatz et al. |
| 5,976,174 | A | 11/1999 | Ruiz |
| 6,024,756 | A | 2/2000 | Huebsch et al. |
| 6,056,760 | A | 5/2000 | Koike et al. |
| 6,117,159 | A | 9/2000 | Huebsch et al. |
| 6,123,715 | A | 9/2000 | Amplatz |
| 6,174,322 | B1 | 1/2001 | Schneidt |
| 6,214,029 | B1 | 4/2001 | Thill et al. |
| 6,221,092 | B1 | 4/2001 | Koike et al. |
| 6,270,515 | B1 | 8/2001 | Linden et al. |
| 6,312,446 | B1 | 11/2001 | Huebsch et al. |
| 6,346,074 | B1 | 2/2002 | Roth |
| 6,355,052 | B1 | 3/2002 | Neuss et al. |
| 6,368,339 | B1 | 4/2002 | Amplatz |
| 6,379,368 | B1 | 4/2002 | Corcoran et al. |
| 6,447,531 | B1 | 9/2002 | Amplatz |
| 6,468,303 | B1 | 10/2002 | Amplatz et al. |
| 6,482,224 | B1 | 11/2002 | Michler et al. |
| 6,488,706 | B1 | 12/2002 | Solymar |
| 6,548,569 | B1 | 4/2003 | Williams et al. |
| 6,551,344 | B2 | 4/2003 | Thill |
| 6,579,393 | B2 | 6/2003 | Tiegs et al. |
| 6,596,013 | B2 | 7/2003 | Yang et al. |
| 6,599,308 | B2 | 7/2003 | Amplatz |
| 6,641,557 | B1 | 11/2003 | Frazier et al. |
| 6,645,225 | B1 | 11/2003 | Atkinson |
| 6,656,206 | B2 | 12/2003 | Corcoran et al. |
| 6,682,546 | B2 | 1/2004 | Amplatz |
| 6,702,835 | B2 | 3/2004 | Ginn |
| 6,712,836 | B1 | 3/2004 | Berg et al. |
| 6,776,784 | B2 | 8/2004 | Ginn |
| 6,838,493 | B2 | 1/2005 | Williams et al. |
| 6,867,247 | B2 | 3/2005 | Williams et al. |
| 6,911,037 | B2 | 6/2005 | Gainor et al. |
| 6,939,348 | B2 | 9/2005 | Malecki et al. |
| 6,960,220 | B2 | 11/2005 | Marino et al. |
| 6,960,224 | B2 | 11/2005 | Marino et al. |
| 6,994,094 | B2 | 2/2006 | Schwartz |
| 7,115,110 | B2 | 10/2006 | Frazier et al. |
| 7,115,135 | B2 | 10/2006 | Corcoran et al. |
| 7,128,073 | B1 | 10/2006 | Van Der Burg et al. |
| 7,144,410 | B2 | 12/2006 | Marino et al. |
| 7,152,605 | B2 | 12/2006 | Khairkhahan et al. |
| 7,165,552 | B2 | 1/2007 | Deem et al. |
| 7,186,251 | B2 | 3/2007 | Malecki et al. |
| 7,192,435 | B2 | 3/2007 | Corcoran et al. |
| 7,192,439 | B2 | 3/2007 | Khairkhahan et al. |
| 7,220,265 | B2 | 5/2007 | Chanduszko et al. |
| 7,226,466 | B2 | 6/2007 | Opolski |
| 2003/0028213 | A1 | 2/2003 | Thill et al. |
| 2003/0045901 | A1 | 3/2003 | Opolski |
| 2003/0130713 | A1 | 7/2003 | Stewart et al. |
| 2003/0144694 | A1 | 7/2003 | Chanduszko et al. |
| 2003/0208232 | A1 | 11/2003 | Blaeser et al. |
| 2003/0225421 | A1 | 12/2003 | Peavey et al. |
| 2004/0073242 | A1 | 4/2004 | Chanduszko |
| 2004/0093017 | A1 | 5/2004 | Chanduszko |
| 2004/0098042 | A1 | 5/2004 | Devellian et al. |
| 2004/0098121 | A1 | 5/2004 | Opolski |
| 2004/0133230 | A1 | 7/2004 | Carpenter et al. |
| 2004/0133236 | A1 | 7/2004 | Chanduszko |
| 2004/0176799 | A1 | 9/2004 | Chanduszko et al. |
| 2004/0220596 | A1 | 11/2004 | Frazier et al. |
| 2004/0230185 | A1 | 11/2004 | Malecki et al. |
| 2004/0243122 | A1 | 12/2004 | Auth et al. |
| 2004/0267191 | A1 | 12/2004 | Gifford, III et al. |
| 2004/0267306 | A1 | 12/2004 | Blaeser et al. |
| 2005/0034735 | A1 | 2/2005 | Deem et al. |
| 2005/0043759 | A1 | 2/2005 | Chanduszko |
| 2005/0055050 | A1 | 3/2005 | Alfaro |
| 2005/0059984 | A1 | 3/2005 | Chanduszko et al. |
| 2005/0065547 | A1 | 3/2005 | Reed et al. |
| 2005/0065548 | A1 | 3/2005 | Marino et al. |
| 2005/0070923 | A1 | 3/2005 | McIntosh |
| 2005/0070957 | A1 | 3/2005 | Das |
| 2005/0075665 | A1 | 4/2005 | Brenzel et al. |
| 2005/0085843 | A1 | 4/2005 | Opolski et al. |
| 2005/0101984 | A1 | 5/2005 | Chanduszko et al. |
| 2005/0113868 | A1 | 5/2005 | Devellian et al. |
| 2005/0119675 | A1 | 6/2005 | Adams et al. |
| 2005/0131460 | A1 | 6/2005 | Gifford, III et al. |
| 2005/0187568 | A1 | 8/2005 | Klenk et al. |
| 2005/0192627 | A1 | 9/2005 | Whisenant et al. |
| 2005/0228434 | A1 | 10/2005 | Amplatz et al. |
| 2005/0234509 | A1 | 10/2005 | Widomski et al. |
| 2005/0251154 | A1 | 11/2005 | Chanduszko et al. |
| 2005/0256532 | A1 | 11/2005 | Nayak et al. |
| 2005/0267495 | A1 | 12/2005 | Ginn et al. |
| 2005/0267523 | A1 | 12/2005 | Devellian et al. |
| 2005/0267524 | A1 | 12/2005 | Chanduszko |
| 2005/0267525 | A1 | 12/2005 | Chanduszko |
| 2005/0267526 | A1 | 12/2005 | Wahr et al. |
| 2005/0267556 | A1 | 12/2005 | Shuros et al. |
| 2005/0273119 | A1 | 12/2005 | Widomski et al. |
| 2005/0273124 | A1 | 12/2005 | Chanduszko |
| 2005/0273135 | A1 | 12/2005 | Chanduszko et al. |
| 2005/0277982 | A1 | 12/2005 | Marino et al. |
| 2005/0288706 | A1 | 12/2005 | Widomski et al. |
| 2005/0288786 | A1 | 12/2005 | Chanduszko |
| 2006/0009800 | A1 | 1/2006 | Christianson et al. |
| 2006/0018948 | A1 | 1/2006 | Guire et al. |
| 2006/0027241 | A1 | 2/2006 | Malecki et al. |
| 2006/0036282 | A1 | 2/2006 | Wahr et al. |
| 2006/0036284 | A1 | 2/2006 | Blaeser et al. |
| 2006/0052821 | A1 | 3/2006 | Abbott et al. |
| 2006/0074410 | A1 | 4/2006 | Malecki et al. |
| 2006/0095052 | A1 | 5/2006 | Chambers |
| 2006/0106420 | A1 | 5/2006 | Dolan et al. |
| 2006/0106447 | A1 | 5/2006 | Opolski |
| 2006/0116710 | A1 | 6/2006 | Corcoran et al. |
| 2006/0122646 | A1 | 6/2006 | Corcoran et al. |
| 2006/0135962 | A1* | 6/2006 | Kick .................. A61M 25/09 606/108 |
| 2006/0229491 | A1 | 10/2006 | Sharkey et al. |
| 2006/0241581 | A1 | 10/2006 | Malecki et al. |
| 2006/0241582 | A1 | 10/2006 | Malecki et al. |
| 2006/0241583 | A1 | 10/2006 | Malecki et al. |
| 2006/0241584 | A1 | 10/2006 | Malecki et al. |
| 2006/0241687 | A1 | 10/2006 | Glaser et al. |
| 2006/0241690 | A1 | 10/2006 | Amplatz et al. |

(56) References Cited

U.S. PATENT DOCUMENTS

| | | |
|---|---|---|
| 2006/0247612 A1 | 11/2006 | Malecki et al. |
| 2006/0247680 A1 | 11/2006 | Amplatz et al. |
| 2006/0276779 A1 | 12/2006 | Malecki et al. |
| 2006/0276839 A1 | 12/2006 | McGuckin, Jr. |
| 2006/0276846 A1 | 12/2006 | Malecki et al. |
| 2007/0005079 A1 | 1/2007 | Zarbatany et al. |
| 2007/0010806 A1 | 1/2007 | Malecki et al. |
| 2007/0010851 A1 | 1/2007 | Chanduszko et al. |
| 2007/0055333 A1 | 3/2007 | Forde et al. |
| 2007/0060858 A1 | 3/2007 | Sogard et al. |
| 2007/0066993 A1 | 3/2007 | Kreidler |
| 2007/0073315 A1 | 3/2007 | Ginn et al. |
| 2007/0073337 A1* | 3/2007 | Abbott ............. A61B 17/12122 606/213 |
| 2007/0078485 A1 | 4/2007 | Deem et al. |
| 2007/0083232 A1 | 4/2007 | Lee |
| 2007/0088388 A1 | 4/2007 | Opolski et al. |
| 2007/0093804 A1 | 4/2007 | Kaveckis et al. |
| 2007/0093805 A1 | 4/2007 | Auth et al. |
| 2007/0106214 A1 | 5/2007 | Gray et al. |
| 2007/0106327 A1 | 5/2007 | Thill et al. |
| 2007/0112347 A1 | 5/2007 | Malecki et al. |
| 2007/0112358 A1 | 5/2007 | Abbott et al. |
| 2007/0112381 A1 | 5/2007 | Figulla et al. |
| 2007/0112382 A1 | 5/2007 | Thill et al. |
| 2007/0118176 A1 | 5/2007 | Opolski et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0129755 A1 | 6/2007 | Abbott et al. |
| 2007/0129756 A1 | 6/2007 | Abbott et al. |
| 2007/0167980 A1 | 7/2007 | Figulla et al. |
| 2007/0167981 A1 | 7/2007 | Opolski et al. |
| 2007/0179583 A1 | 8/2007 | Goetzinger et al. |
| 2008/0243081 A1* | 10/2008 | Nance ................ A61B 17/3439 604/164.03 |
| 2017/0056176 A1* | 3/2017 | Rowe .................... A61F 2/2454 |
| 2017/0224323 A1* | 8/2017 | Rowe ................. A61B 17/0057 |
| 2017/0224483 A1* | 8/2017 | Kizuka ................. A61F 2/2466 |
| 2017/0239041 A1* | 8/2017 | Quinn ................. A61F 2/2466 |
| 2017/0265994 A1* | 9/2017 | Krone ...................... A61F 2/243 |
| 2018/0055636 A1* | 3/2018 | Valencia ................... A61F 2/24 |
| 2018/0256327 A1* | 9/2018 | Perszyk ................ A61F 2/2436 |
| 2018/0311473 A1* | 11/2018 | Laby ................ A61M 25/0113 |

FOREIGN PATENT DOCUMENTS

| | | |
|---|---|---|
| WO | 2005082255 A1 | 9/2005 |
| WO | 2008027869 A2 | 3/2008 |
| WO | 2015066150 A1 | 5/2015 |

\* cited by examiner

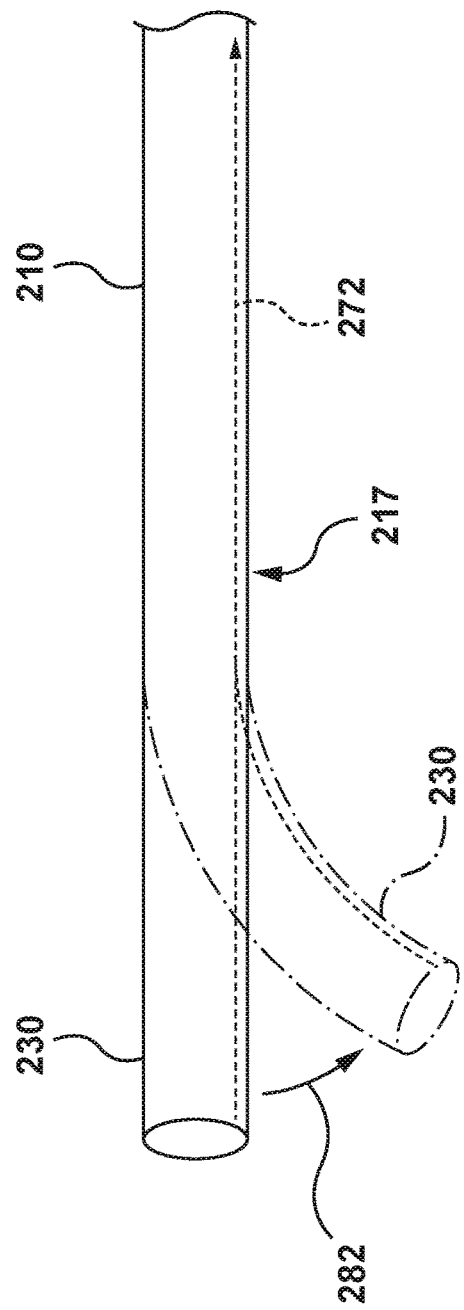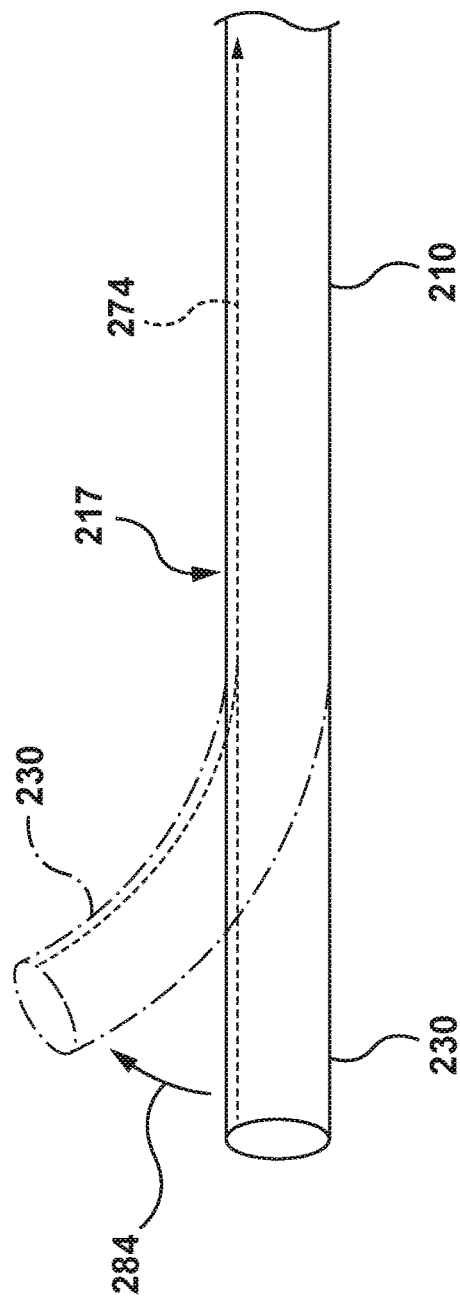

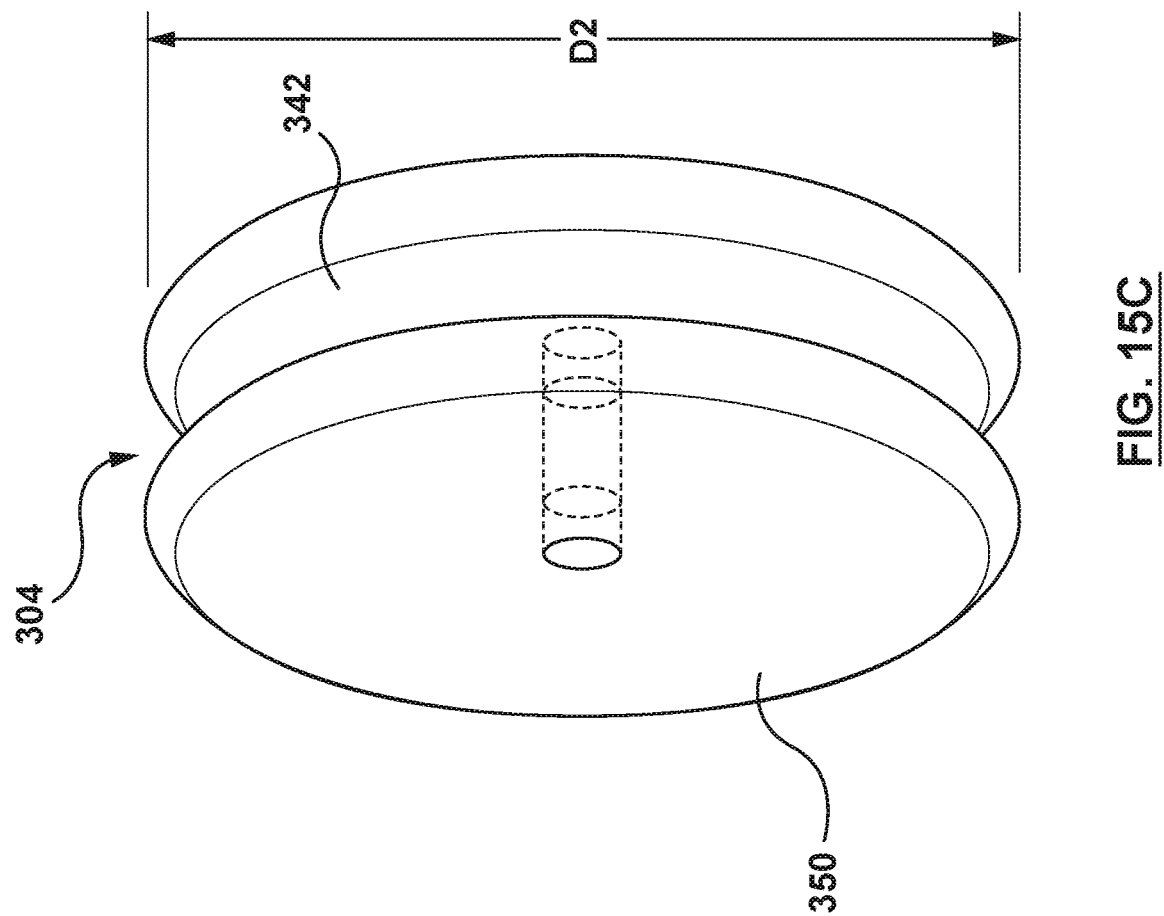

SYSTEMS AND METHODS FOR PERCUTANEOUSLY SUPPORTING AND MANIPULATING A SEPTAL WALL

CROSS-REFERENCE TO RELATED APPLICATIONS

This application claims the benefit under 35 U.S.C. § 119(e) of U.S. Provisional Application No. 62/586,993 filed Nov. 16, 2017, the contents of which are incorporated by reference herein in their entirety.

FIELD OF THE INVENTION

The present technology relates to transseptal apparatus and procedures utilized for delivering a prosthesis or other therapy to the site of a native heart valve. More specifically, the present invention relates to a catheter-based system having a flanged device for supporting and manipulating or articulating a septal wall, e.g., an interatrial septum, of a heart during a transseptal approach to a native heart valve, e.g., a mitral valve.

BACKGROUND OF THE INVENTION

The human heart is a four chambered, muscular organ that provides blood circulation through the body during a cardiac cycle. The four main chambers include the right atria and right ventricle which supplies the pulmonary circulation, and the left atria and left ventricle which supplies oxygenated blood received from the lungs to the remaining body. To ensure that blood flows in one direction through the heart, atrioventricular valves (tricuspid and mitral valves) are present between the junctions of the atria and the ventricles, and semi-lunar valves (pulmonary valve and aortic valve) govern the exits of the ventricles leading to the lungs and the rest of the body. These valves contain leaflets or cusps that open and shut in response to blood pressure changes caused by the contraction and relaxation of the heart chambers. The leaflets move apart from each other to open and allow blood to flow downstream of the valve, and coapt to close and prevent backflow or regurgitation in an upstream manner.

Diseases associated with heart valves, such as those caused by damage or a defect, can include stenosis and valvular insufficiency or regurgitation. For example, valvular stenosis causes the valve to become narrowed and hardened which can prevent blood flow to a downstream heart chamber from occurring at the proper flow rate and may cause the heart to work harder to pump the blood through the diseased valve. Valvular insufficiency or regurgitation occurs when the valve does not close completely, allowing blood to flow backwards, thereby causing the heart to be less efficient. A diseased or damaged valve, which can be congenital, age-related, drug-induced, or in some instances, caused by infection, can result in an enlarged, thickened heart that loses elasticity and efficiency. Some symptoms of heart valve diseases can include weakness, shortness of breath, dizziness, fainting, palpitations, anemia and edema, and blood clots, which can increase the likelihood of stroke or pulmonary embolism. Symptoms can often be severe enough to be debilitating and/or life threatening.

Heart valve prostheses have been developed for repair and replacement of diseased and/or damaged heart valves. Such heart valve prostheses can be percutaneously delivered and deployed at the site of the diseased heart valve through catheter-based systems. Heart valve prostheses can be delivered while in a low profile or compressed/collapsed arrangement so that the heart valve prosthesis can be advanced through the patient's vasculature. Once positioned at the treatment site, the heart valve prosthesis can be expanded to engage tissue at the diseased heart valve region to, for instance, hold the heart valve prosthesis in position. While these heart valve prostheses offer minimally invasive methods for heart valve repair and/or replacement, challenges remain to providing effective, less invasive, smaller crossing profile valve prosthesis delivery systems, particularly for mitral valve replacement. For repair and replacement of a native mitral valve, it may be desirable in some circumstances for a clinician to utilize a transseptal approach to the native mitral valve with a catheter-based delivery system. However, challenges exist with maneuvering a catheter-based delivery system within the confined space of the left atrium that may limit a clinician's ability to properly position a heart valve prosthesis at the native mitral valve when using a transseptal approach. More specifically, a mitral valve prosthesis may be up to 39 mm in length and between 23 F-24 F in crossing profile and the length and crossing profile of the mitral valve prosthesis retained within the delivery system can create challenges during a transseptal approach to the native mitral valve. Sharp bends or angles as a delivery system containing such a mitral valve prosthesis crosses from the right atrium, thorough a transseptal puncture in the interatrial septum, into the left atrium and then immediately downward to the left ventricle may be difficult to negotiate. Moreover, the sharp angle between an axis of the transseptal puncture and the native mitral valve require at least a distal segment of the delivery catheter that contains the prosthesis to be articulated or bent/curved to align with the native mitral valve, potentially tearing or otherwise damaging the tissue of the fragile interatrial septum around the transseptal puncture point during articulation.

Accordingly, there remains a need in the art for catheter-based systems and methods for use with transseptal approaches to a native mitral valve that address one or more of the deficiencies noted above.

BRIEF SUMMARY OF THE INVENTION

Embodiment hereof are directed to a catheter-based system for percutaneously supporting and manipulating or articulating a septal wall of a heart. The catheter-based system includes a catheter and a flanged device. The flanged device is disposed at a distal end of the catheter. The flanged device is coupled to a distal portion of the catheter and includes a proximal anchor and a distal anchor. The flanged device has a radially collapsed configuration for delivery within a vasculature and a radially expanded configuration. When the flanged device is in the radially expanded configuration and is disposed through a transseptal puncture in the septal wall, the flanged device is configured to support and manipulate or articulate the septal wall of the heart.

Embodiments hereof are also directed to a method of delivering, positioning, and manipulating or articulating a flanged device for percutaneously supporting and manipulating or articulating a septal wall of a heart. A distal portion of a catheter, with the flanged device secured thereto, is advanced through a transseptal puncture in the septal and into a first chamber of the heart to position a distal anchor of the flanged device within the first chamber of the heart. The distal anchor is transitioned from a collapsed state to an expanded state. The catheter is proximally retracted to position a proximal surface of the distal anchor adjacent to and engaged with the septal wall in the first chamber and to position a proximal anchor of the flanged device within a second chamber of the heart. The proximal anchor is transitioned from a collapsed state to an expanded state with a distal surface of the proximal anchor being adjacent to and engaged with the septal wall in the second chamber. The catheter may be distally advanced such that the flanged device manipulates or articulates the septal wall. Alternatively, or in combination with distal advancement of the catheter, a distal end portion of the catheter may be articulated and/or deflected such that the flanged device manipulates or articulates the septal wall. An auxiliary medical device may then be advanced through the catheter to treat a native heart valve. When the treatment is complete, the auxiliary medical device may then be removed from the catheter. The catheter may then be proximally retracted and/or the deflection of the distal end of the catheter is removed such that the flanged device manipulates or articulates the septal wall to permit the septal wall to return to a native shape.

BRIEF DESCRIPTION OF DRAWINGS

The foregoing and other features and aspects of the present technology can be better understood from the following description of embodiments and as illustrated in the accompanying drawings. The accompanying drawings, which are incorporated herein and form a part of the specification, further serve to illustrate the principles of the present technology. The components in the drawings are not necessarily to scale.

FIG. 2D is a side view illustration of a distal portion of a catheter-based system configured in accordance with an embodiment hereof.

FIG. 2E is a side view illustration of a distal portion of a catheter-based system configured in accordance with an embodiment hereof.

FIG. 15C is a perspective illustration of the flanged device of FIG. 15A, wherein the flanged device is in the radially expanded configuration.

DETAILED DESCRIPTION OF THE INVENTION

Specific embodiments of the present invention are now described with reference to the figures, wherein like reference numbers indicate identical or functionally similar elements. The terms "distal" and "proximal", when used in the following description to refer to a catheter and/or other system components hereof are with respect to a position or direction relative to the treating clinician. Thus, "distal" and "distally" refer to positions distant from or in a direction away from the treating clinician, and the terms "proximal" and "proximally" refer to positions near or in a direction toward the treating clinician. The terms "distal" and "proximal", when used in the following description to refer to a native vessel or a native valve are with reference to the direction of blood flow. Thus, "distal" and "distally" refer to positions in a downstream direction with respect to the direction of blood flow and the terms "proximal" and "proximally" refer to positions in an upstream direction with respect to the direction of blood flow.

The following detailed description is merely exemplary in nature and is not intended to limit the present technology or the application and uses of the present technology. Although the description of embodiments hereof is in the context of treatment of heart valves and particularly in the context of gaining percutaneous access to a mitral valve via a transseptal approach, the present technology may also be used in any other body passageways where it is deemed useful. Furthermore, there is no intention to be bound by any expressed or implied theory presented in the preceding technical field, background, brief summary or the following detailed description.

Figure 1:
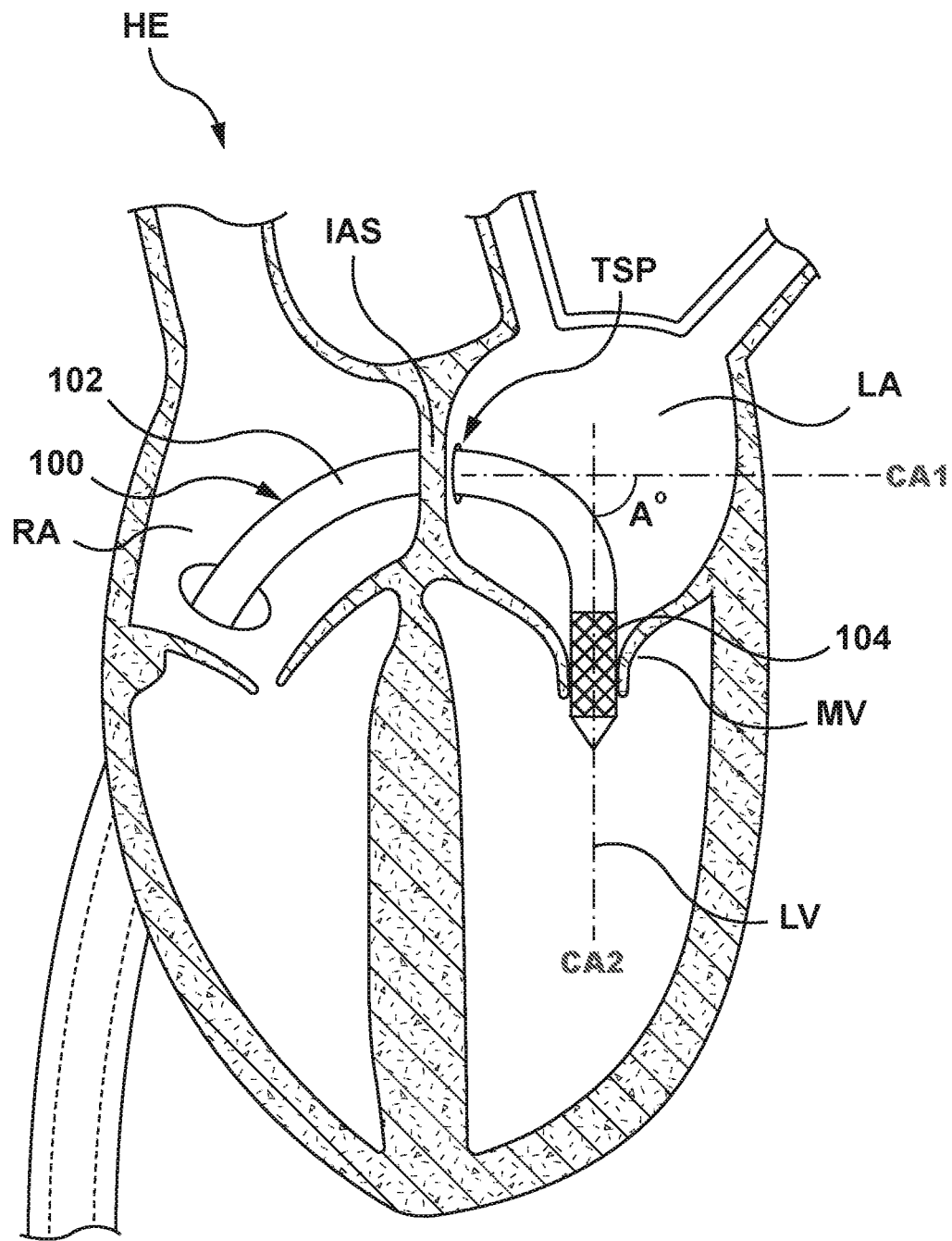
FIG. 1 is a sectional cut-away illustration of a heart illustrating a transseptal approach to a native mitral valve, wherein an angle between a first central axis of a transseptal puncture and a second central axis of a native mitral valve is illustrated.

FIG. 1 is a cutaway view of a heart HE illustrating a transseptal approach to a native mitral valve MV. A delivery system 100 includes a delivery catheter 102 and a heart valve prosthesis 104. The delivery system 100 is advanced through the vasculature of a patient using established percutaneous transcatheter procedures. The delivery system 100 is advanced first into a right atrium RA, through a transseptal puncture TSP in an interatrial septum IAS, into a left atrium LA, then downward, through the native mitral valve MV into a left ventricle LV. The delivery system 100 must make a sharp turn within the left atrium LA to align itself with the native mitral valve MV. This sharp turn, bend, or curve has an angle A° that may approach 90° between a first central axis CA1 that extends through the transseptal puncture TSP in the interatrial septum IAS and a second central axis CA2 that extends through the native mitral valve MV, as shown in FIG. 1. The sharpness of the turn may produce challenges in aligning the delivery system 100 with the native mitral valve MV. Movement of the delivery system 100 to properly align the heart valve prosthesis 104 with the native mitral valve MV places stress on the interatrial septum IAS at the transseptal puncture TSP as the delivery system 100 is manipulated or articulated. This stress on the interatrial septum IAS may result in damage to the interatrial septum IAS such as tearing of tissue around the transseptal puncture TSP. Moreover, proper alignment of the heart valve prosthesis 104 is difficult, time consuming, and may jeopardize the successful deployment of the heart valve prosthesis 104.

Figure 9:
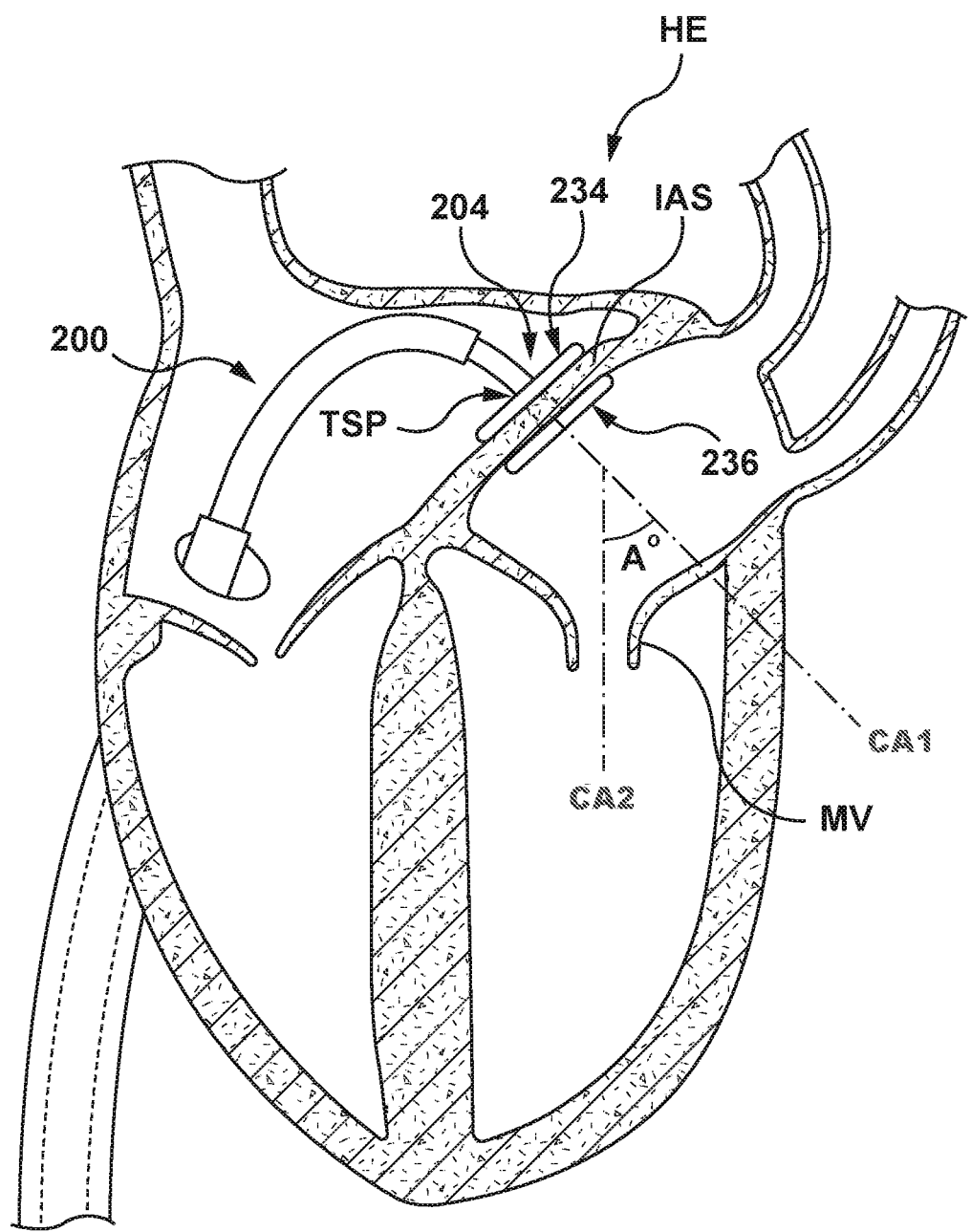
FIG. 9 is an illustration of the catheter-based system of FIG. 2A in situ, wherein the catheter-based system has been distally advanced to manipulate or articulate the interatrial septum to better align a first central axis of a transseptal puncture of the interatrial septum with a second central axis of the native mitral valve.

A catheter-based system in accordance with embodiments hereof includes a catheter and a flanged device. The catheter generally includes a handle, and an inner shaft. In an embodiment, the flanged device is removably coupled to a distal end of the inner shaft. The flanged device is configured to traverse the septal wall, e.g. an interatrial septum, of a heart via a transseptal puncture when the flanged device is in a radially collapsed configuration. The flanged device is further configured to percutaneously support the septal wall, e.g. the interatrial septum, about the transseptal puncture when the flanged device is in a radially expanded configuration. Once in the radially expanded configuration, the catheter-based system is configured to manipulate or articulate the interatrial septum of the heart to deform the interatrial septum and establish a more favorable path to the native mitral valve. As used herein, "more favorable path" is meant to convey that an angle A° between a first central axis CA1 (in FIG. 1) extending through the transseptal puncture and a second central axis CA2 (in FIG. 1) extending through the native mitral valve with the interatrial septum manipulated or articulated (as shown in FIG. 9) is less than the angle A° between the first central axis CA1 extending through the transseptal puncture and the second central axis CA2 extending through the native mitral valve when the interatrial septum is not manipulated or articulated (as shown in FIG. 1). Moreover, with manipulation and/or articulation of the flanged device, the overall bend radius of the catheter can be increased such that a delivery system with a heart valve prosthesis in a radially collapsed configuration disposed therein can more easily traverse from the right atrium to the left atrium and into the left ventricle of the heart through the catheter-based system. In one embodiment, the bend radius may be <37 mm to achieve acceptable alignment with the native mitral valve.

FIGS. 2A-3C illustrate a catheter-based system 200 according to an embodiment hereof. The catheter-based system 200 includes a catheter 202 and a flanged device 204 at a distal portion thereof. The catheter-based system 200 is configured to percutaneously support and manipulate or articulate an interatrial septum of a heart according to embodiments hereof.

Figure 2A:
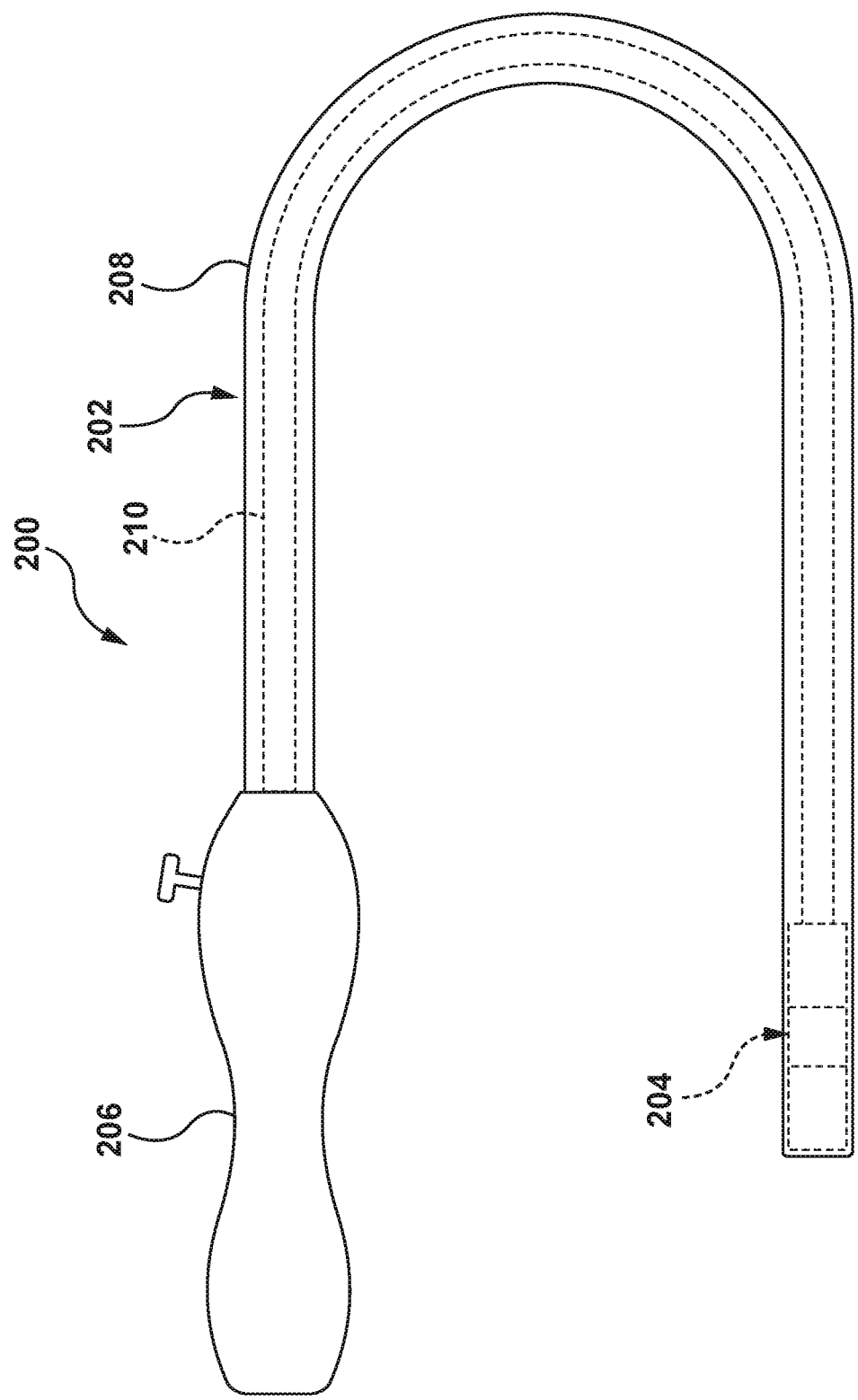
FIG. 2A is a side view illustration of a catheter-based system configured in accordance with an embodiment hereof, wherein a flanged device is mounted at a distal portion thereof and the flanged device is shown in a radially collapsed configuration for delivery.
Figure 2B:
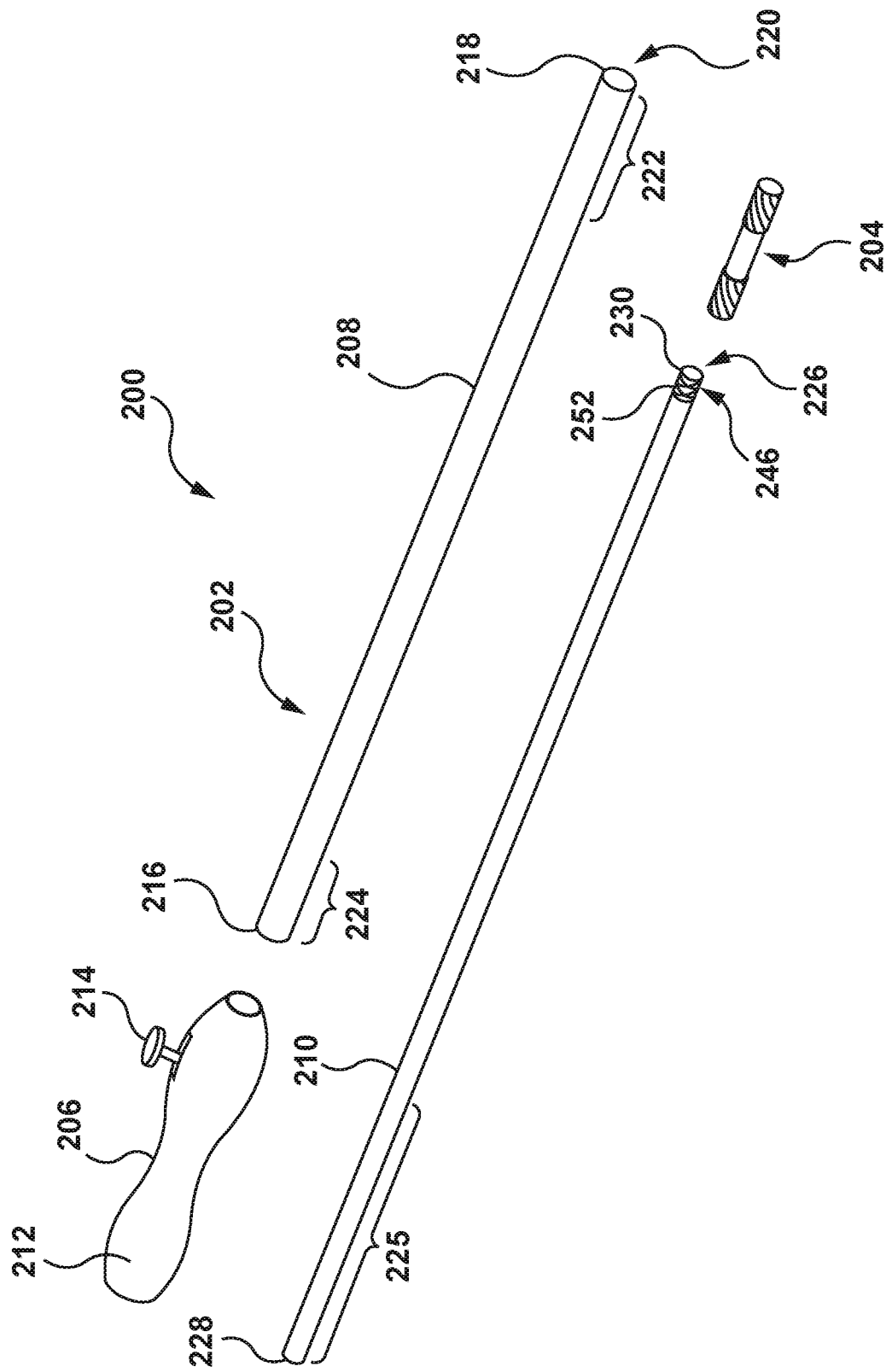
FIG. 2B is an exploded perspective view illustration of the catheter-based system of FIG. 2A.

Referring to the illustrations of FIGS. 2A and 2B, in an embodiment, the catheter 202 includes a handle 206, an outer sheath 208, and an inner shaft 210. The catheter 202 is configured to deliver, deploy, and manipulate or articulate the flanged device 204. The components of the catheter 202 may assume different forms and construction based upon application requirements as described in greater detail in, for example, U.S. Pat. No. 8,876,893 to Dwork et al., which is incorporated by reference in its entirety, herein.

Referring to FIG. 2B, the handle 206 includes a housing 212 and an outer sheath actuator or actuation mechanism 214 that may be manipulated by a user. The handle 206 provides a surface for convenient handling and grasping by a user, and while the handle 206 of FIGS. 2A and 2B is shown with a cylindrical shape, this is by way of example and not limitation as other shapes and sizes may be used. Further, while the handle 206 is shown with a specific style of outer sheath actuation mechanism 214, this is also by way of example and not limitation, and various actuation mechanisms may be utilized including, but not limited to an axially-slidable lever, a rotary rack and pinion gear, a button, a knob, a thumbwheel, a switch, a toggle, or other applicable actuation mechanisms. The handle 206 can have a variety of configurations described in greater detail in, for example, U.S. Pat. No. 8,579,963 to Tabor, which is incorporated by reference in its entirety, herein.

As also shown in FIG. 2B, the outer sheath 208 of the catheter 202 includes a proximal end 216, a distal end 218, and a lumen or passageway 220. The passageway 220 extends from the proximal end 216 to the distal end 218 of the outer sheath 208 and is configured to receive the inner shaft 210. The outer sheath 208 is coaxial and slidably disposed over the inner shaft 210 and the flanged device 204. A distal portion 222 of the outer sheath 208 is configured to retain the flanged device 204 in the radially collapsed configuration for delivery to a treatment site, such as the interatrial septum of the heart. While the distal portion 222 is described herein as a distal portion of the outer sheath 208, in an embodiment the distal portion 222 may be a separate component coupled to the distal end 218 of the outer sheath 208. Moreover, although the outer sheath 208 is described herein as a single component, this is by way of example and not limitation, and the outer sheath 208 may include multiple components such as, but not limited to proximal and distal sheaths or other components suitable for the purposes described herein. The proximal end 216 is configured for fixed connection to the handle 206. In an embodiment, the proximal end 216 of the outer sheath 208 extends proximally into the housing 212 of the handle 206, and a proximal portion 224 of the outer sheath 208 is operably coupled to the outer sheath actuation mechanism 214 of the handle 206. The proximal portion 224 is operably coupled to the outer sheath actuation mechanism 214 such that movement of the outer sheath actuation mechanism 214 causes the outer sheath 208 and the distal portion 222 to move relative to the inner shaft 210 and the handle 206. However, if the outer sheath actuation mechanism 214 is not actuated and the handle 206 is manipulated, the outer sheath 208 moves with the handle 206, not relative to the handle 206. The outer sheath 208 may be constructed or formed, either along the entire length of the outer sheath 208 or in various segments, of one or more materials such as, but not limited to polyurethane (e.g. Peliethane©, Elasthane$^{TM}$, Texin®, Tecothane®), polyamide polyether block copolymer (e.g. Pebax®, nylon 12), polyethylene, nylon, polyester, polyimide, polyethylene terephthalate (PET), polyetheretherketone (PEEK), or other materials suitable for the purposes of the present disclosure. In addition, the walls of the outer sheath 208 may be reinforced with a variety of structures, such as metal braids or coils. Such reinforcements may be along the entire length of the outer sheath 208 or in various segments. The proximal portion 224 of the outer sheath 208 may be coupled to the outer sheath actuator mechanism 214 of the handle 206, for example, and not by way of limitation, by adhesives, welding, bonding, clamping, or other coupling methods as appropriate. In some embodiments, the handle 206 may include a numerical or graphical display of information indicating the amount of movement the outer sheath 208 and the distal portion 222 move relative to the inner shaft 210 and the handle 206.

Also shown in FIG. 2B, the inner shaft 210 of the catheter 202 extends within the passageway 220 of the outer sheath 208. The inner shaft 210 includes a lumen or passageway 226 extending from a proximal end 228 to a distal end 230 of the inner shaft 210. The passageway 226 is sized to receive an auxiliary medical device such as, but not limited to a delivery system for a heart valve prosthesis. The distal end 230 of the inner shaft 210 is coupled to the flanged device 204, and the inner shaft 210 is configured to manipulate the flanged device 204, coupled thereto. At least a portion 225 of the inner shaft 210 extends within the housing 212 of the handle 206 and is coupled to the handle 206. During sliding or longitudinal movement of the outer sheath 208 relative thereto, the inner shaft 210 is fixed relative to the handle 206. The inner shaft 210 may be constructed or formed, either along the entire length of the inner shaft 210 or in various segments, of one or more materials such as but not limited to polyurethane (e.g. Peliethane©, Elasthane$^{TM}$, Texin®, Tecothane®), polyamide polyether block copolymer (e.g. Pebax®, nylon12), polyethylene, nylon, polyester, polyimide, polyethylene terephthalate (PET), polyetheretherketone (PEEK), or other materials suitable for the purposes described herein. In addition, the walls of the inner shaft 210 may be reinforced with a variety of structures, such as metal braids or coils. Such reinforcements may be along the entire length of the inner shaft 210 or in various segments. The inner shaft 210 may be coupled to the handle 206 by adhesives, welding, clamping, or other coupling methods as appropriate. The inner shaft 210 can assume a variety of configurations described in greater detail in, for example, U.S. Pat. No. 8,579,963 to Tabor, previously incorporated by reference herein.

Figure 2C:
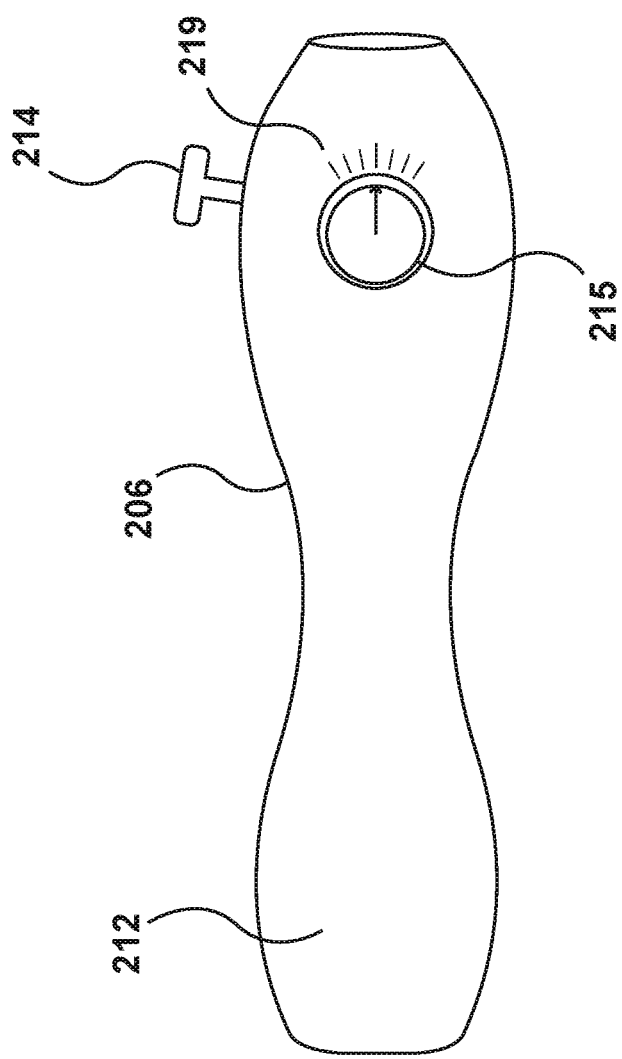
FIG. 2C is a side view illustration of a handle of a catheter-based system configured in accordance with an embodiment hereof.
Figure 2F:
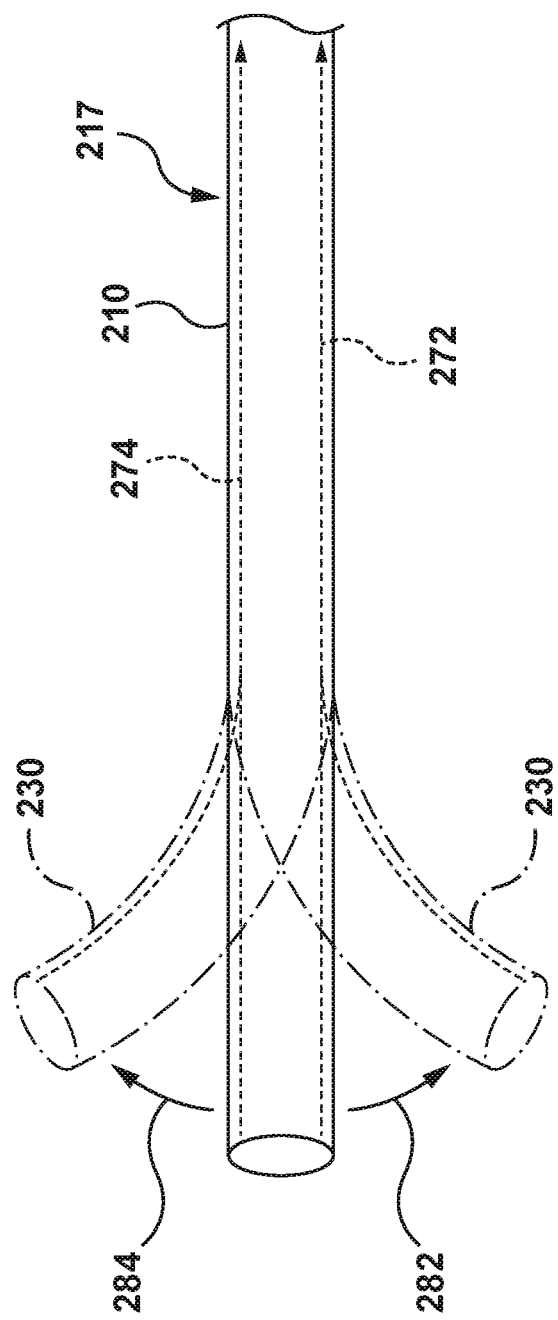
FIG. 2F is a side view illustration of a distal portion of a catheter-based system configured in accordance with an embodiment hereof.

In some embodiments, the inner shaft 210 is deflectable and the handle 206 includes one or more inner shaft deflection actuators 215 to actuate one or more inner shaft deflection mechanisms 217. The inner shaft deflection actuators 215 may be manipulated by a user to deflect, for example, the distal end 230 of the inner shaft 210. While the handle 206 is shown in FIG. 2C with a specific type of deflection actuator 215, this is by way of example and not limitation. The deflection actuators 215 may have any suitable form including buttons, knobs, thumbwheels, levers, switches, toggles, or other devices. One or more deflection mechanisms 217 may be actuated by one or more deflection actuators 215 to deflect, bend, arc, or reshape the inner shaft 210, such as to form a curve along one or more portions of the inner shaft 210. In addition, in some embodiments, one or more locking actuators (not shown) may be used to actuate locking mechanisms (not shown) to lock the inner shaft 210 in the desired shape. Locking actuators may have any suitable form including buttons, knobs, thumbwheels, levers, switches, toggles, or other devices. In some embodiments, the handle 206 may include a numerical or graphical display 219 of information indicating the degree of deflection of the inner shaft 210.

Figure 2G:
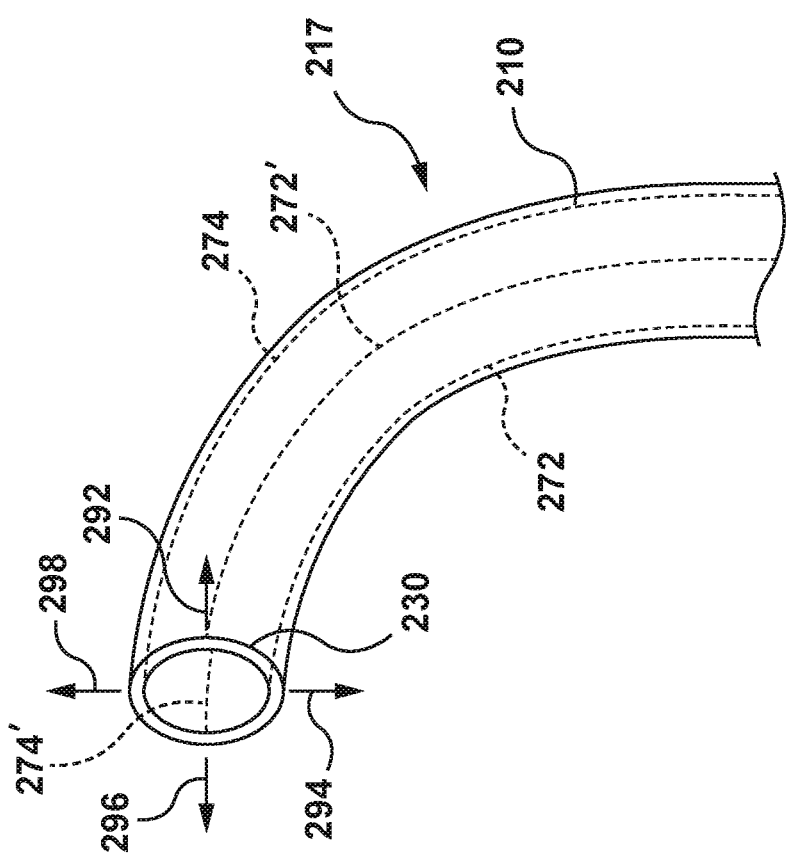
FIG. 2G is a side view illustration of a distal portion of a catheter-based system configured in accordance with an embodiment hereof.

In some embodiments, one or more deflection mechanisms 217 comprise one or more cables or pullwires within the wall of the inner shaft 210. As shown in FIG. 2D, the inner shaft 210 may include a pullwire 272 slidably disposed in a lumen within the wall of the inner shaft 210 extending to the distal end 230. By applying tension to the pullwire 272 in the proximal direction, the distal end 230 curves or deflects in the direction of the pullwire 272 as illustrated by arrow 282. Likewise, as shown in FIG. 2E, placement of the pullwire 274 along the opposite side of the inner shaft 210 will allow the distal end 230 to curve or deflect in the opposite direction, as illustrated by arrow 284, when tension is applied to the pullwire 274. Thus, referring to FIG. 2F, diametrically opposing placement of pullwires 272, 274 within the walls of the inner shaft 210 allows the distal end 230 to be deflected in opposite directions. This provides a means of correcting or adjusting a curvature. For example, if tension is applied to one pullwire to create a curvature, the curvature may be lessened by applying tension to the diametrically opposite pullwire. Referring now to FIG. 2G, an additional set of opposing pullwires 272', 274' may extend within the wall of the inner shaft 210 as shown. This combination of pullwires 272, 272', 274, 274' allows curvature of the distal end 230 in at least four directions illustrated by arrows 292, 294, 296, 298.

Any number of cables or pullwires and associated lumens may be placed in any arrangement, singly or in pairs, symmetrically or asymmetrically. This may allow curvature in any direction and about various axes. The cables or pullwires may be fixed at any location along the length of the inner shaft 210 by any suitable method, such as gluing, tying, soldering, or potting, for example. When tension is applied to the pullwire, the curvature forms from the point of attachment of the pullwire toward the proximal direction. Therefore, curvatures may be formed throughout the length of the catheter depending upon the locations of the points of attachment of the pullwires. Typically, however, the pullwires will be attached near the distal end 230 of the inner shaft 210.

In some embodiments, the inner shaft 210 may be precurved rather than deflectable or in addition to being deflectable, the inner shaft 210 may be comprised of a polymer or copolymer which can be set in a desired curvature, such as by heat setting. Likewise, the inner shaft 210 may be comprised of a shape-memory alloy.

Figure 3A:
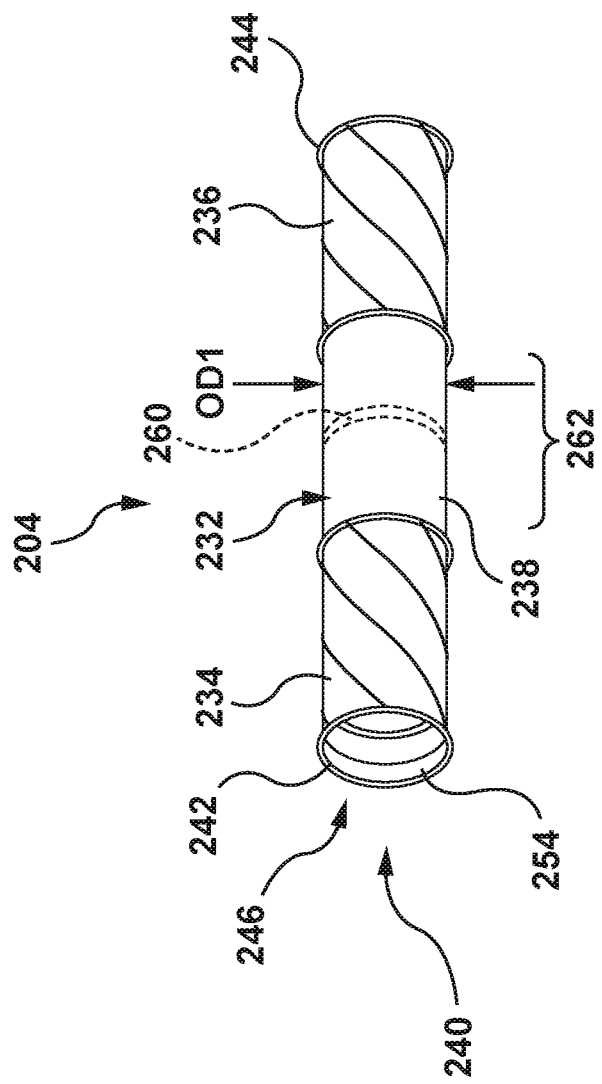
FIG. 3A is a perspective illustration of the flanged device of the catheter-based system of FIG. 2A configured in accordance with an embodiment hereof, wherein the flanged device is in the radially collapsed configuration.
Figure 3C:
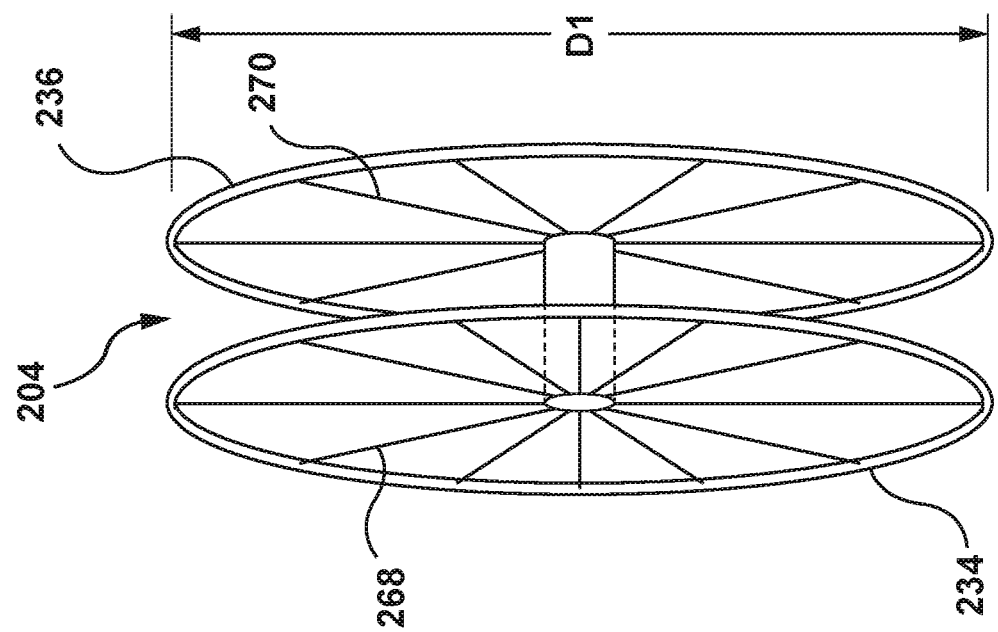
FIG. 3C is a perspective illustration of the flanged device of FIG. 3A, wherein the flanged device is in the radially expanded configuration.
Figure 3B:
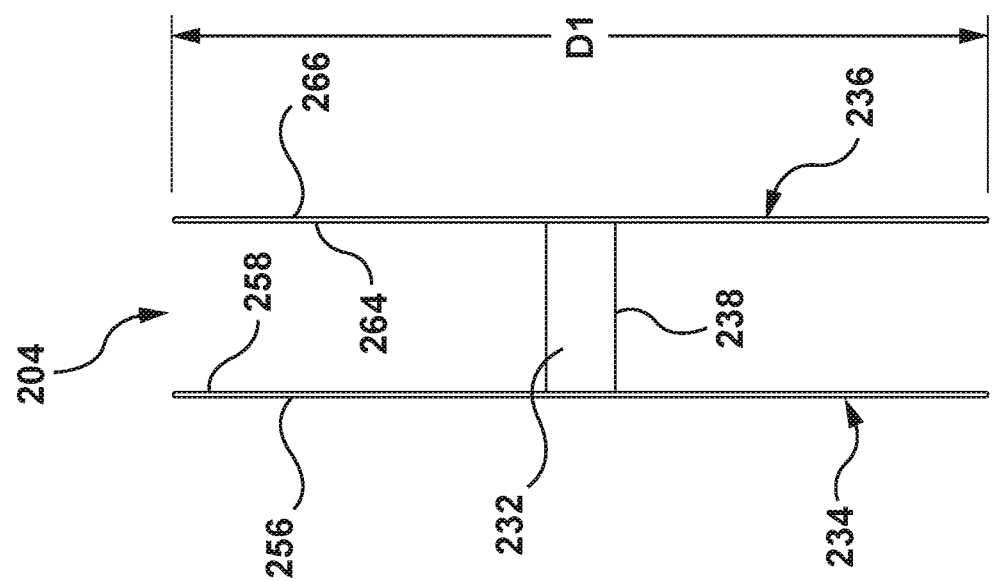
FIG. 3B is a side view illustration of the flanged device of FIG. 3A, wherein the flanged device is in a radially expanded configuration.

FIGS. 3A-3C illustrate the flanged device 204 according to an embodiment hereof. The flanged device 204 includes a flanged device shaft 232, a proximal anchor or umbrella 234, and a distal anchor or umbrella 236, as shown in FIG. 3A. The flanged device 204 includes a radially collapsed configuration for delivery to the interatrial septum of the heart, as shown in FIG. 3A. The flanged device 204 further includes a radially expanded configuration for supporting and manipulating or articulating the interatrial septum, as shown in FIG. 3B. When the flanged device 204 is in the radially expanded configuration of FIG. 3B, the proximal anchor 234 is in an expanded state and the distal anchor 236 is in an expanded state. More specifically, when the flanged device 204 is positioned within a heart and is in the radially expanded configuration, the proximal anchor 234 may be disposed within the right atrium in the expanded state and the distal anchor 236 may be disposed within the left atrium in the expanded state. When the flanged device 204 is in the expanded state and positioned across an interatrial septum, the proximal anchor 234 and the distal anchor 236 may be disposed on opposite sides of the interatrial septum, and the flanged device 204 is configured to support and manipulate or articulate the interatrial septum of the heart without damaging the interatrial septum. In an embodiment, the flanged device 204 is further configured to be removably coupled to the catheter 202. In an embodiment, when the flanged device 204 is in the radially expanded configuration and disposed across the interatrial septum and uncoupled from the catheter 202, the flanged device 204 is configured to seal the transseptal puncture in the interatrial septum through which the flanged device 204 is disposed, as described below.

The flanged device shaft 232 of the flanged device 204 is a generally tubular structure with a constant outside diameter OD1, and includes a shaft wall 238 and a central lumen or central passageway 240, as shown in FIG. 3A. The flanged device shaft 232 includes a proximal end 242 and a distal end 244, and the central lumen 240 extends from the proximal end 242 to the distal end 244 thereof. The central lumen 240 is sized to receive auxiliary medical devices such as a delivery system for a mitral valve prosthesis. The central lumen 240 is configured such that when the flanged device 204 is removably coupled to the inner shaft 210, the passageway 226 of the inner shaft 210 and the central lumen 240 of the flanged device shaft 232 are aligned to form a continuous passageway extending from the proximal end 228 of the inner shaft 210 to the distal end 244 of the flanged device shaft 232. The flanged device shaft 232 further includes a length 262. The length 262 is disposed between the proximal and distal anchors 234, 236 to space the proximal anchor 234 from the distal anchor 236. The length 262 of the flanged device shaft 232 is sized to traverse a puncture in an interatrial septum. The length 262 of the flanged device shaft 232 is configured to support the interatrial septum at a puncture when disposed there-through, as described below. In the embodiment of FIG. 3A, the flanged device shaft 232 further includes a sealing mechanism 260, described below. The sealing mechanism 260 is disposed within the central lumen 240 and coupled thereto. The flanged device shaft 232 may be formed of materials such as but not limited to polyethylene, polyether block amide (PEBA), nickel-titanium alloy (e.g. NITINOL), stainless steel, or other materials suitable for the purposes described herein.

In the embodiments of FIGS. 2A 2B, and 3A-3C, the flanged device shaft 232 is removably coupled to the distal end 230 of the inner shaft 210 by a coupling mechanism 246. In an embodiment, the coupling mechanism 246 is a threaded coupling mechanism. The coupling mechanism 246 is configured to removably couple the distal end 230 of the inner shaft 210 to the proximal end 242 of the flanged device shaft 232. The coupling mechanism 246 includes a plurality of threads 252 on an outer surface of a distal portion of the inner shaft 210, as shown in FIG. 2B, and a corresponding plurality of threads 254 on an inner surface of a proximal portion of the flanged device shaft 232, as shown in FIG. 3A. The plurality of threads 254 of the flanged device shaft 232 are configured to receive and engage the corresponding plurality of threads 252 of the inner shaft 210 such that the flanged device 204 may be removably coupled to the inner shaft 210 of the catheter 202. Stated more plainly, the coupling mechanism 246 is configured such that rotation of the inner shaft 210 in a first direction couples the inner shaft 210 to the flanged device 204, and rotation of the inner shaft 210 in a second direction opposite the first direction uncouples the inner shaft 210 from the flanged device 204. While the inner shaft 210 and the flanged device shaft 232 are each shown with a specific number, pitch, and handedness of the plurality of threads 252, 254, respectively, this is not meant to limit the invention, and the plurality of threads 252, 254 of the inner shaft 210 and the flanged device shaft 232, respectively, may be of a greater or lesser number, with a greater or lesser pitch, and a different handedness.

Figure 3D:
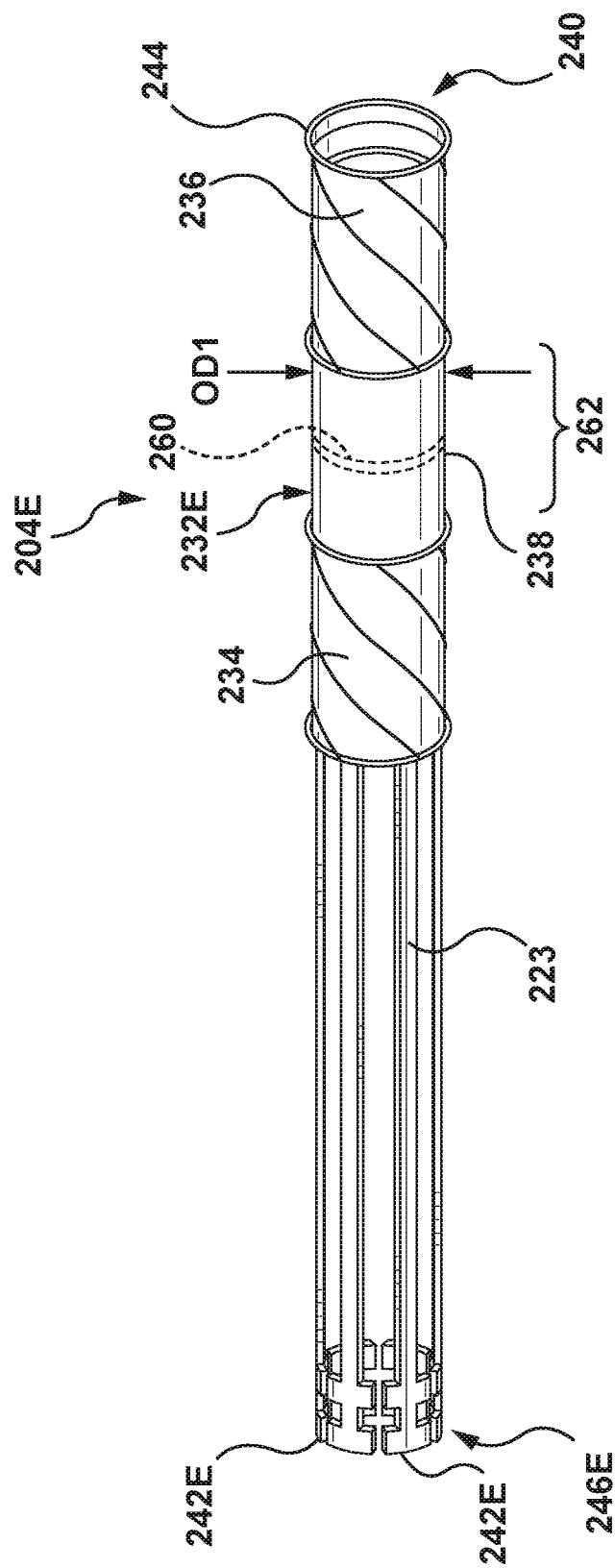
FIG. 3D is a perspective illustration of a flanged device configured in accordance with an embodiment hereof, wherein the flanged device is in the radially collapsed configuration.
Figure 3E:
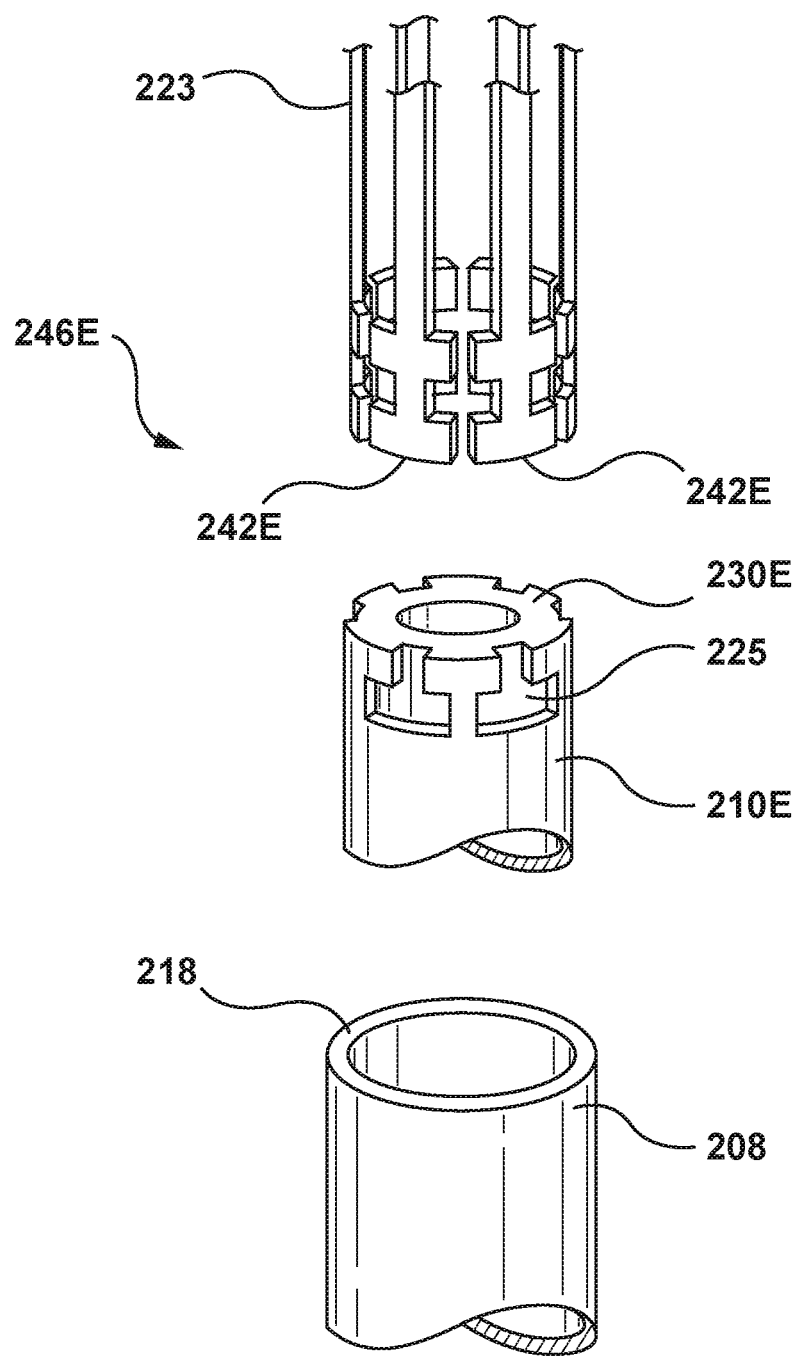
FIG. 3E is an exploded perspective view illustration of portions of a catheter-based system configured in accordance with an embodiment hereof having the flanged device of FIG. 3D.
Figure 3F:
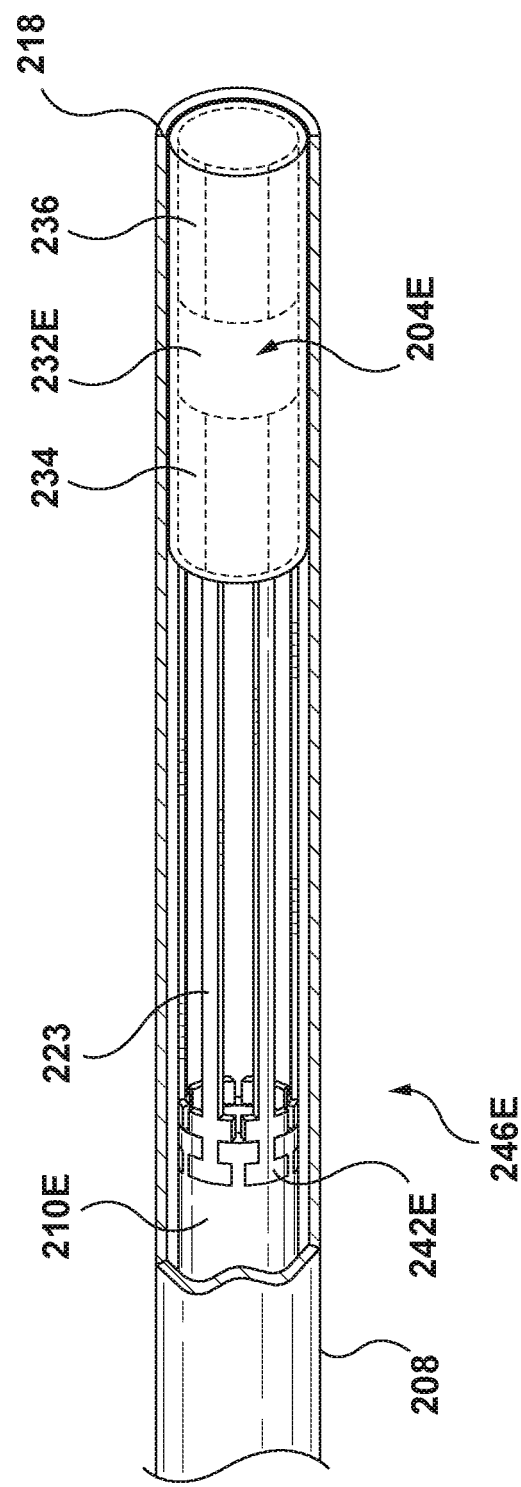
FIG. 3F is a side view illustration of a distal portion of the catheter-based system of FIG. 3E, wherein the flanged device is mounted at a distal portion thereof and the flanged device is shown in a radially collapsed configuration for delivery.
Figure 3G:
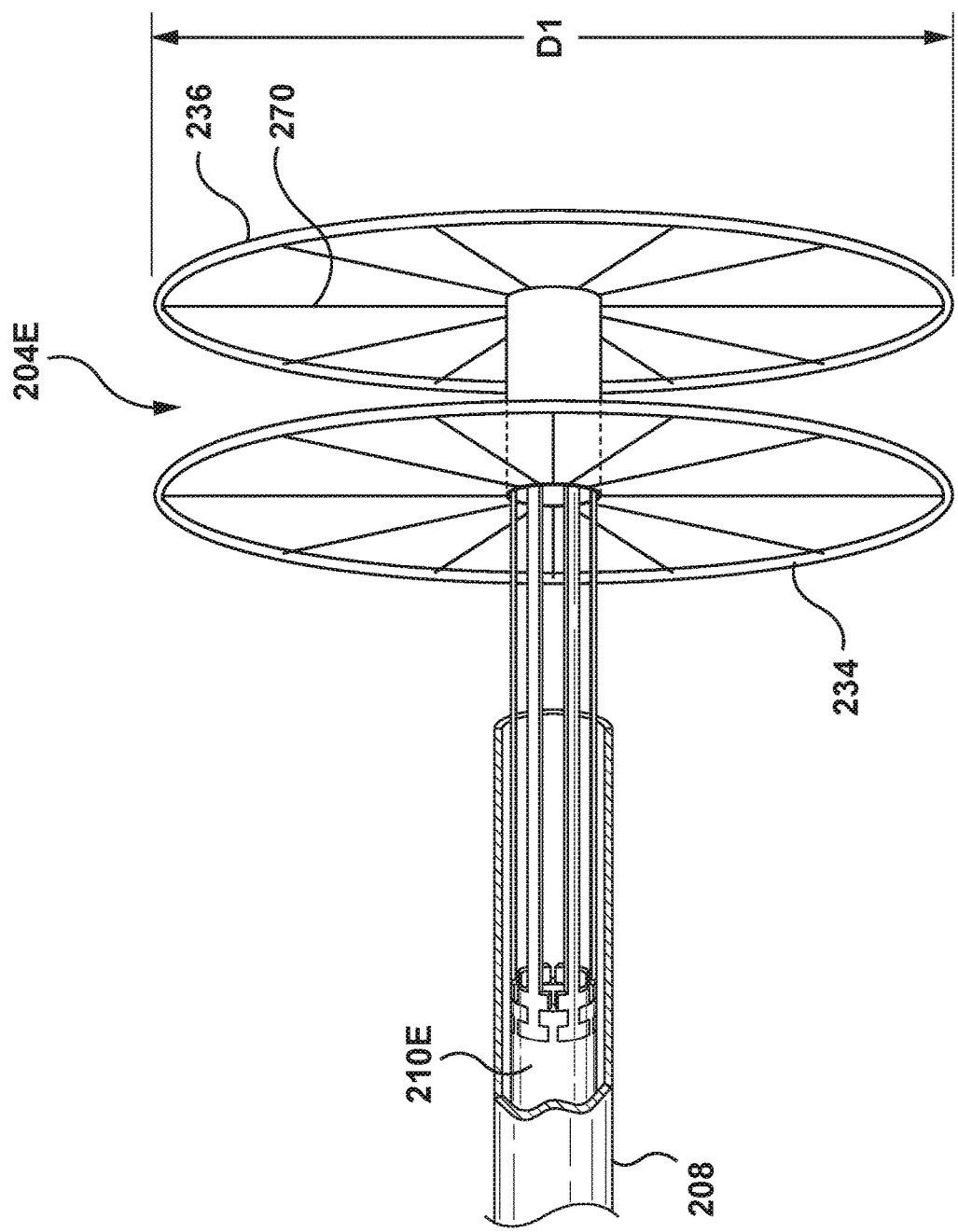
FIG. 3G is a side view illustration of the distal portion of the catheter-based system of FIG. 3E, wherein the flanged device is shown in a radially expanded configuration during delivery.

In another embodiment, a coupling mechanism 246E can include one or more coupling arms 223 and matching coupling grooves 225, as shown in FIGS. 3D-3H in which features unchanged from prior embodiments retain the same reference numbers. A flanged device 204E may include a flanged device shaft 232E having one or more arms 223 extending proximal of a proximal anchor 234 of the flanged device 204E. As shown in FIGS. 3E-3G, a distal end 230E of an inner shaft 210E can include one or more grooves 225 matching the shape of proximal ends 242E of the arms 223. Preferably the number of grooves 225 of the inner shaft 210E matches the number of arms 223 of the flanged device 204E. As illustrated in FIG. 3F, when the flanged device 204E is located within the outer sheath 208, the proximal ends 242E of the arms 223 are set within the grooves 225 of the inner shaft 210E, thereby releasably attaching the flanged device 204E to the inner shaft 210E.

In some embodiments, the coupling mechanism 246 can include one or more elongate tension members, such as one or more sutures, chords, or filaments, extending the length of the inner shaft 210 (not shown). The elongate tension members can be slidably disposed in one or more lumens within the wall of the inner shaft 210 and the elongate tension members can be used to couple the flanged device shaft 232 to the distal end 230 of the inner shaft 210. The elongate tension members can be looped through the flanged device shaft 232 so that tensioning the elongate tension members fixedly couples the flanged device 204 to the inner shaft 210. To release the flanged device 204 from the inner shaft 210, one end of each of the elongate tension members is released and the other end is pulled until the elongate tension members are removed from the flanged device 204 thus releasing the flanged device 204 from the inner shaft 210.

In some embodiments, coupling mechanism 246 may include a snap fit mechanism, a friction fit mechanism, or any other coupling mechanism suitable to removably couple the inner shaft 210 to the flanged device shaft 232 for the purposes described herein.

The proximal anchor 234 of the flanged device 204 includes a proximal surface 256 and a distal surface 258, as shown in FIG. 3B. The proximal anchor 234 includes a collapsed state, wherein the proximal anchor 234 is radially collapsed for delivery to the interatrial septum of the heart, as shown in FIG. 3A. The proximal anchor 234 further includes the expanded state, as shown in FIGS. 3B and 3C. When in the expanded state, the proximal anchor 234 radially expands to a general disc or flat cylindrical shape, as shown in FIG. 3C. The distal surface 258 of the proximal anchor 234 is configured for engagement with a second side, opposite the first side, of the septal wall, which in this embodiment is the interatrial septum of the right atrium, when the proximal anchor 234 is in the expanded state and the flanged device 204 is disposed at a transseptal puncture in the interatrial septum. The proximal anchor 234 in the expanded state and engaged with the interatrial septum in the right atrium is further configured to support the interatrial septum and to transmit forces applied to the proximal anchor 234 of the flanged device 204 across a large surface area of the interatrial septum engaged with the distal surface 258 of the proximal anchor 234. The proximal anchor 234 is coupled to or extends from an outer surface of a proximal portion of the shaft wall 238 of the flanged device shaft 232 proximal of and spaced from the distal anchor 236. The proximal anchor 234 is formed of a shape memory material with a pre-set shape in the expanded state. The proximal anchor 234 is of a suitable diameter D1, such that forces applied to the proximal anchor 234 may be distributed over a large surface area of the adjacent interatrial septum such that the interatrial septum is not damaged during manipulation or articulation. In a non-limiting example, the diameter D1 of the proximal anchor 234 may be from 10 mm up to 30 mm. The proximal anchor 234 is self-expanding from the collapsed state to the expanded state. "Self-expanding" as used herein means that a structure/component has a mechanical memory to return to the expanded or deployed configuration or state as described herein. In some embodiments, the proximal anchor 234 may be coupled to the flanged device shaft 232 by methods such as, but not limited to, adhesives, bonding, fusing, welding, or other suitable methods.

In an embodiment, the proximal anchor 234 is formed of a frame 268, as best shown in FIG. 3C. In some embodiments, the frame 268 is part of or an extension of the flanged device shaft 232. The flanged device shaft 232 and the frame 268 can be constructed from a shape memory material that is configured to self-deploy or self-expand when released from the outer sheath 208 of the catheter 202 (not shown in FIGS. 3A-3C). When the proximal anchor 234 is in the expanded state, the frame 268 is configured to provide structural rigidity to the proximal anchor 234 such that forces applied to the proximal anchor 234 may be distributed over the large surface area of the adjacent interatrial septum such that the interatrial septum is not damaged during articulation. While the frame 268 is shown in FIG. 3C with a radial spoke configuration, this is by way of example and not limitation, and the frame 268 may have other configurations, such as, but not limited to various lattice configurations. In some embodiments, the frame 268 may be covered by a braided mesh covering, a woven fabric covering, and/or a tissue covering (not shown in FIG. 3C). The shape-memory of the frame 268 of the proximal anchor 234 may be accomplished with various shape-memory materials, such as, but not limited to a nickel-titanium alloy (e.g. NITINOL), polymers, or other materials suitable for the purposes described herein. A braided mesh covering may be formed of materials such as, but not limited to a nickel-titanium alloy (e.g. NITINOL), stainless steel, or other materials suitable for the purposes described herein. A woven fabric covering may be formed of materials such as, but not limited to a woven Dacron material, a woven polymer material, or other materials suitable for the purposes described herein. A tissue covering may be formed of materials such as, but not limited to a pericardial tissue, a bovine tissue, a porcine tissue, or other materials suitable for the purposes described herein.

The distal anchor 236 is similar to the self-expanding proximal anchor 234 described previously. Accordingly, the distal anchor 236 includes a proximal surface 264 and a distal surface 266, as shown in FIG. 3B. Further, the distal anchor 236 includes a collapsed state, wherein the distal anchor 236 is radially collapsed for delivery to a septal wall, e.g., the interatrial septum, of the heart, as shown in FIG. 3A. The distal anchor 236 further includes an expanded state, as shown in FIGS. 3B and 3C. When the distal anchor 236 is in the expanded state, the distal anchor 236 radially expands to a general disc or flat cylindrical shape, as shown in FIG. 3C. The proximal surface 264 of the distal anchor 236 is configured for engagement with a first side of the septal wall, which in this embodiment is the interatrial septum of the left atrium, when the distal anchor 236 is in the expanded state and the flanged device 204 is disposed at the transseptal puncture of the interatrial septum. The distal anchor 236 is coupled to or extends from the outer surface of a distal portion of the shaft wall 238 of the flanged device shaft 232 distal of and spaced from the proximal anchor 234. Similar to the proximal anchor 234 described previously, the distal anchor 236 is of a suitable diameter D1 such that forces applied to the distal anchor 234 may be distributed over a large surface area of the adjacent interatrial septum such that the interatrial septum is not damaged during articulation. In the embodiment of FIGS. 3A-3C, the distal anchor 236 includes a frame 270. The frame 270 is similar to the frame 268 described previously with reference to the proximal anchor 236. Therefore, details of the construction and alternatives of the frame 270 of the distal anchor 236 will not be repeated. The distal anchor 236 and the frame 270 are shaped and formed of materials and by methods similar to the proximal anchor 234 and the frame 268 described previously. For example, in some embodiments, similar to the frame 268, the frame 270 can be part of or an extension of the flanged device shaft 232.

Figure 3H:
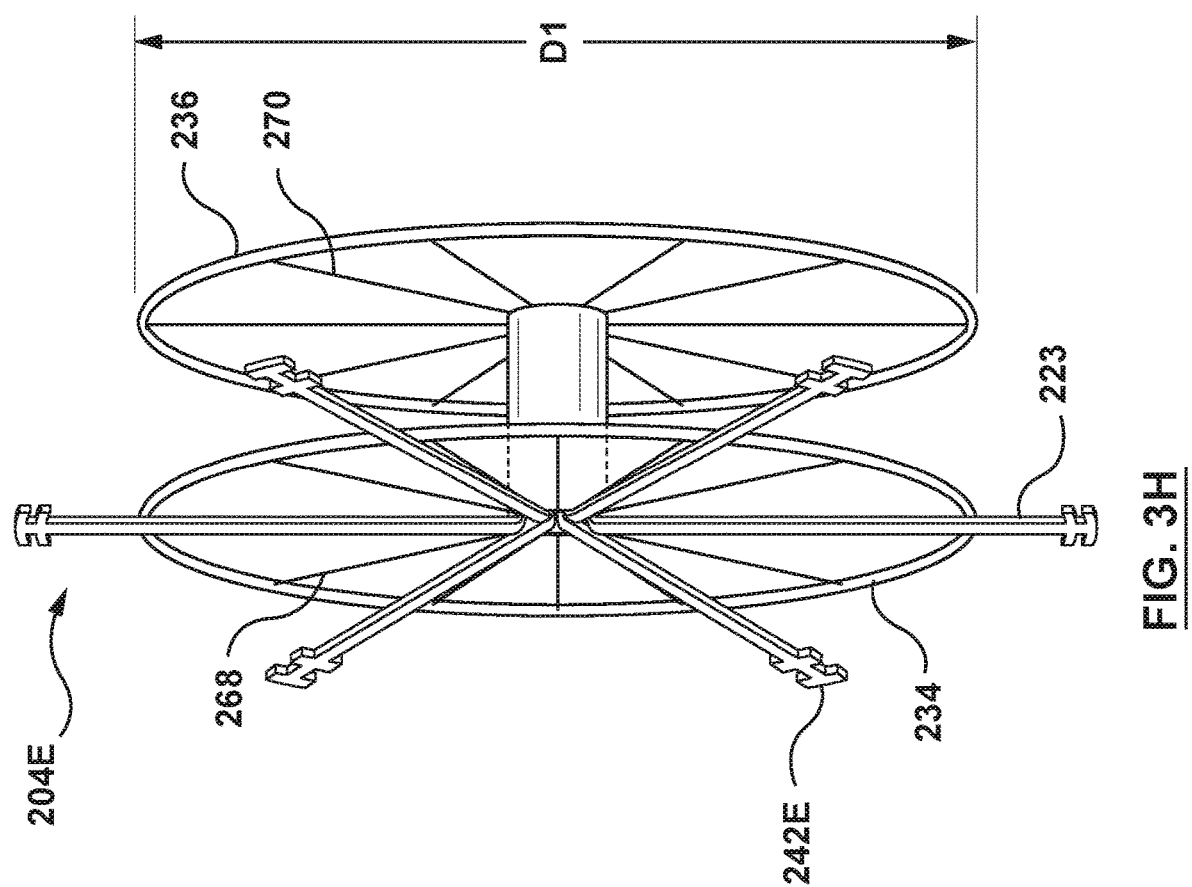
FIG. 3H is a perspective illustration of the flanged device of FIG. 3D, wherein the flanged device is in the radially expanded configuration.

In some embodiments, the flanged device 204E includes the one or more arms 223 that can be self-expanding from a collapsed configuration or state, as shown in FIG. 3D, to an expanded configuration or state, as shown in FIG. 3H. The arms 223 can include a collapsed state, wherein the arms 223 are radially collapsed for delivery to a septal wall, e.g., the interatrial septum, of the heart, as shown in FIG. 3F. The arms 223 further can include an expanded state wherein the arms 223 radially expand to a flat shape, as shown in FIG. 3H. In the expanded state when the flanged device 204E is fully deployed at a transseptal puncture in the interatrial septum, the arms 223 are configured to engage the proximal surface of the proximal anchor 234.

In an embodiment, the flanged device 204 further includes a sealing mechanism 260 disposed within the central lumen 240 of the flanged device shaft 232. The sealing mechanism 260 is disposed distal of the coupling mechanism 246 such that the sealing mechanism 260 does not interfere with the coupling mechanism 246. In an embodiment, the sealing mechanism 260 is a hemostatic seal. The sealing mechanism 260 is configured to receive an auxiliary medical device (not shown in FIGS. 3A-3H) there through, and provide a hemostatic seal with the auxiliary medical device received there through. The sealing mechanism 260 is further configured such that when no auxiliary medical device is received there through, the sealing mechanism 260 does not permit fluid to flow through the central lumen 240. Stated more plainly, the sealing mechanism 260 is configured to seal or occlude the central lumen 240 of the flanged device shaft 232 to prevent fluid flow there-through.

With an understanding of the components of the catheter-based system 200, the interaction of the various components is now described with reference to FIGS. 3F-13. The flanged device 204 of the catheter-based system 200 is manipulated to the radially collapsed configuration and restrained in the radially collapsed configuration by the outer sheath 208 of the catheter 202 that surrounds the flanged device 204, as shown in FIGS. 2A and 3F.

Figure 4:
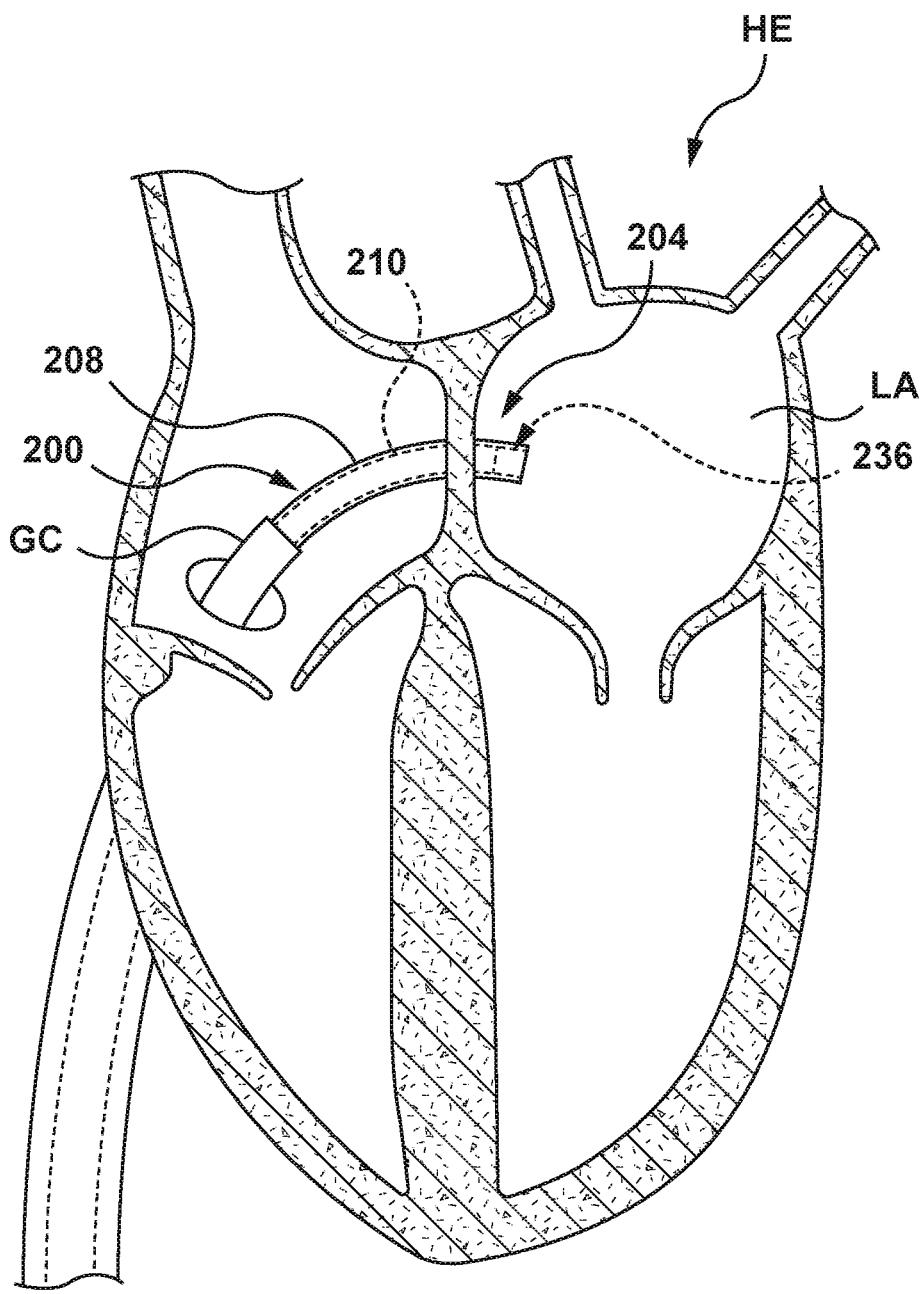
FIG. 4 is an illustration of the catheter-based system of FIG. 2A in situ, wherein a guide catheter is positioned within a right atrium and the catheter-based system is positioned is positioned in the left atrium via a transseptal approach, wherein the flanged device is in a radially collapsed configuration for delivery thereof, in accordance with an embodiment hereof.
Figure 5:
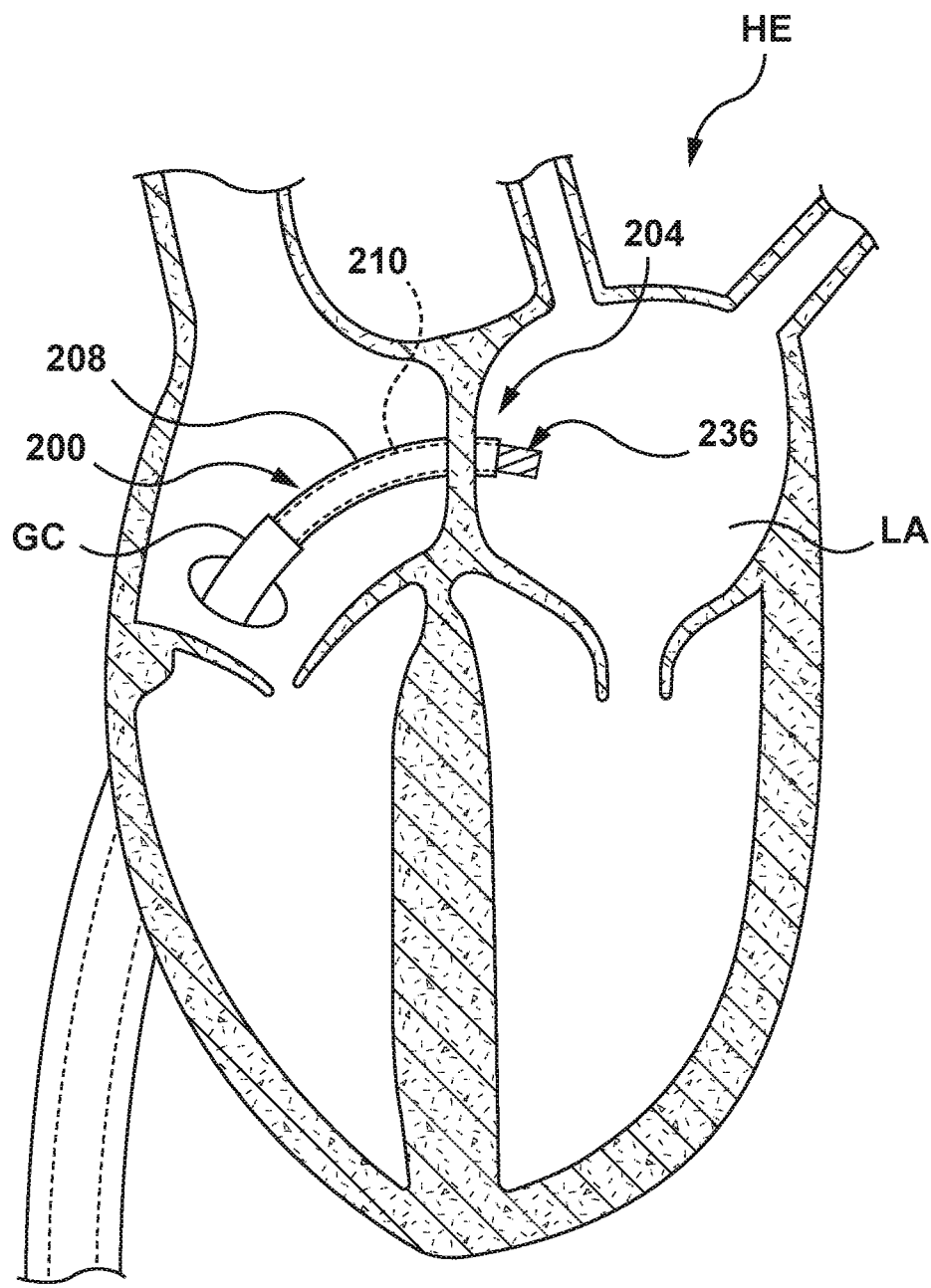
FIG. 5 is an illustration of the catheter-based system of FIG. 2A in situ, wherein an outer sheath of a catheter has been proximally retracted to release a distal anchor.
Figure 6:
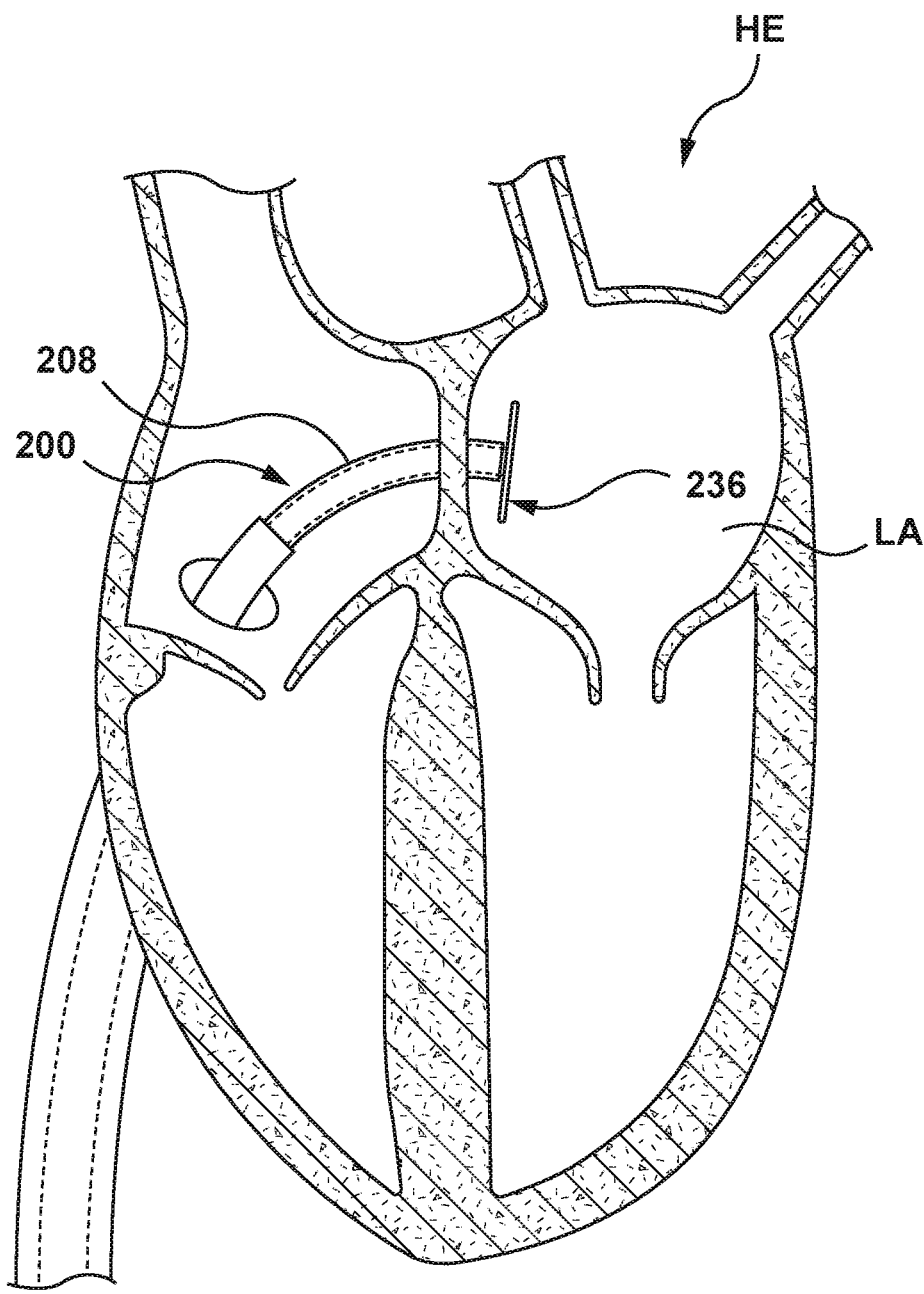
FIG. 6 is an illustration of the catheter-based system of FIG. 2A in situ, wherein the distal anchor has expanded to an expanded state.
Figure 7:
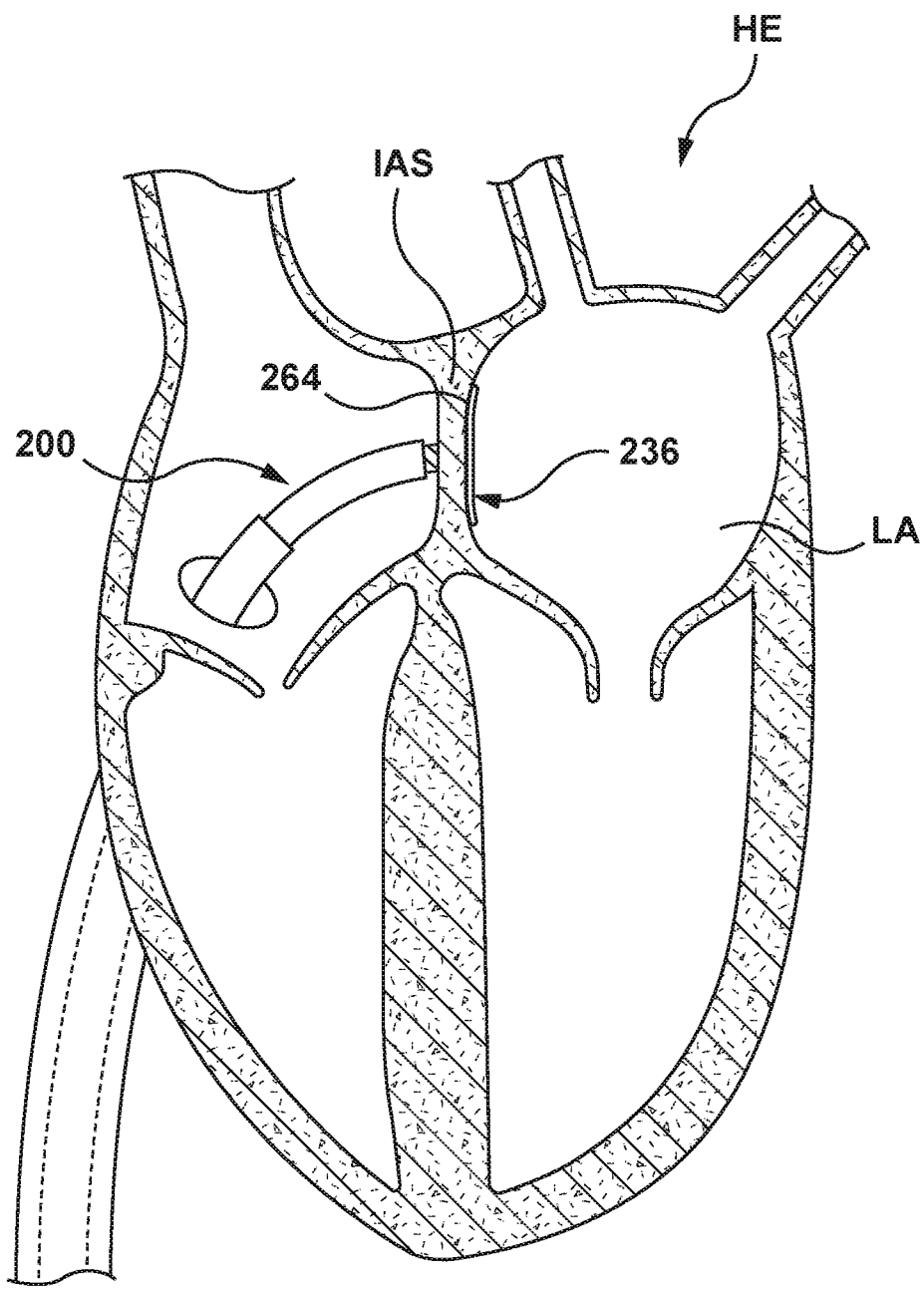
FIG. 7 is an illustration of the catheter-based system of FIG. 2A in situ, wherein the catheter-based system has been proximally retracted to position the distal anchor adjacent the interatrial septum within the left atrium.
Figure 8:
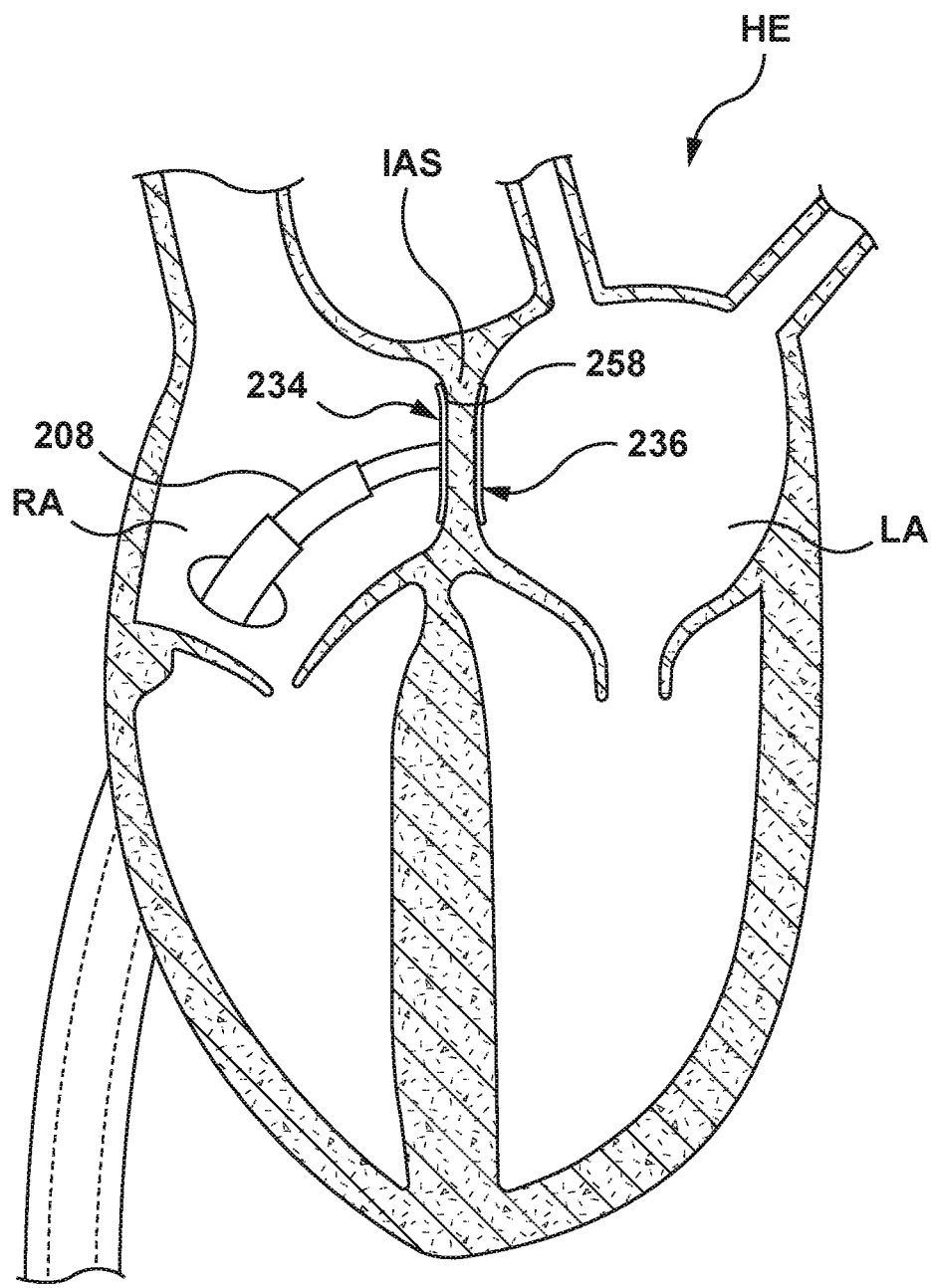
FIG. 8 is an illustration of the catheter-based system of FIG. 2A in situ, wherein the outer sheath of the catheter has been proximally retracted to release a proximal anchor, and the proximal anchor has expanded to an expanded state adjacent the interatrial septum within the right atrium.

The catheter-based system 200 is advanced to a septal wall of a heart, in this embodiment the interatrial septum IAS of the heart, to position the flanged device 204 through or across the interatrial septum, as shown in FIG. 4. Thereafter, the outer sheath 208 of the catheter 202 is proximally retracted to release the distal anchor 236 of the flanged device 204 from the outer sheath, as shown in FIG. 5. The distal anchor 236 radially expands from the collapsed state to the expanded state within a first chamber of the heart, in this embodiment the left atrium LA, as shown in FIG. 6. With the distal anchor 236 in the expanded state, the catheter-based system 200 is proximally retracted to position the proximal surface 264 of the distal anchor 236 adjacent the interatrial septum IAS and to engage the tissue of the interatrial septum within the left atrium, as shown in FIG. 7. With the proximal surface 264 of the distal anchor 236 engaged with the interatrial septum IAS within the left atrium LA, the outer sheath 208 is again proximally retracted to release the proximal anchor 234 within a second chamber of the heart, in this embodiment the right atrium RA, as shown in FIG. 8. The proximal anchor 234 expands from the collapsed state to the expanded state adjacent the interatrial septum within the right atrium, and the distal surface 258 of the proximal anchor 234 engages tissue of the interatrial septum IAS within the right atrium RA. Thus with the flanged device 204 in the radially expanded configuration, a portion of the interatrial septum IAS of the heart HE is disposed or sandwiched between and supported by the proximal and the distal anchors 234, 236 of the flanged device 204.

In some embodiments wherein the flanged device 204E includes one or more coupling arms 223, the outer sheath 208 is proximally retracted just enough to release the proximal anchor 234 but not enough to release the arms 223 from the inner shaft 210E, as shown in FIG. 3G.

With the septal wall, and more specifically the interatrial septum IAS supported on each side by the flanged device 204, the catheter-based system 200 may be distally advanced and/or deflected, as described above, to manipulate or articulate the flanged device 204 and the interatrial septum IAS sandwiched there-between, as shown in FIG. 9. It will be understood that the catheter-based system 200 may be deflectable by various methods understood by those knowledgeable in the pertinent art such as, but not limited to pull wires or other suitable methods, e.g., as described above. The flanged device 204 and the interatrial septum IAS are manipulated or articulated such that the first central axis CA1 that extends through the transseptal puncture TSP in the interatrial septum IAS is more closely aligned with the second central axis CA2 that extends through the native mitral valve MV. Stated another way the angle A° between the first central axis CA1 extending through the transseptal puncture and the second central axis CA2 extending through the native mitral valve with the interatrial septum manipulated or articulated is less than the angle A° (shown in FIG. 1) between the first central axis CA1 extending through the transseptal puncture and the second central axis CA2 extending through the native mitral valve when the interatrial septum is not manipulated or articulated. Thus, manipulation and/or articulation of the flanged device 204 and the interatrial septum reduces the angle A° between the central axes of the transseptal puncture TSP and the native mitral valve MV. Moreover, when the interatrial septum has been manipulated or articulated by the flanged device 204, the bend radius or curve of the catheter-based system 200 is increased and forms a softer, more favorable, and less tortuous path through which a heart valve delivery catheter or other treatment device may be tracked.

Figure 10:
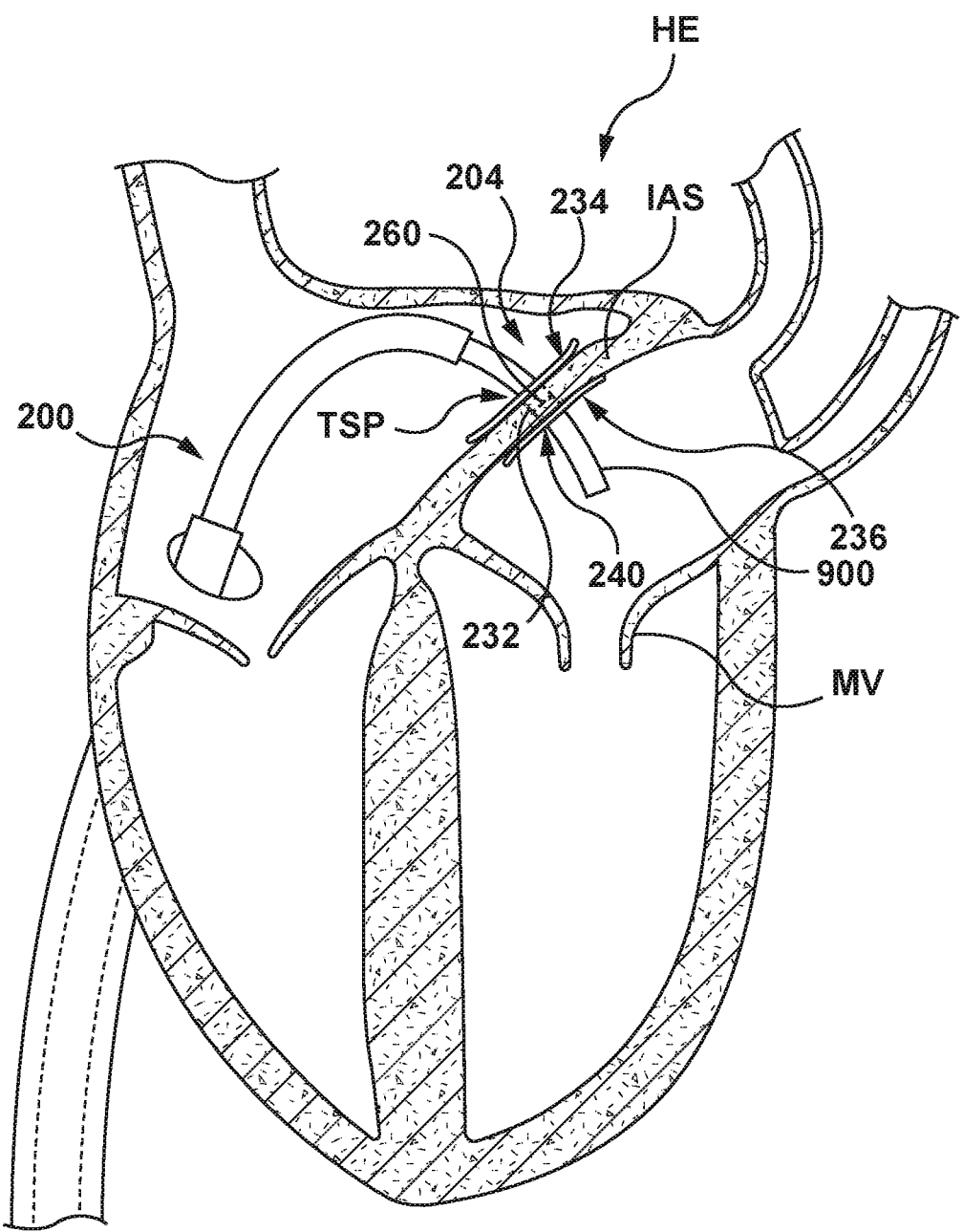
FIG. 10 is an illustration of the catheter-based system of FIG. 2A in situ, wherein an auxiliary medical device has been advanced through the catheter-based system and into the left atrium.

An auxiliary medical device 900, such as a heart valve delivery catheter for delivering, for example, a prosthetic mitral valve in a radially collapsed configuration may now be advanced through the passageway 226 of the inner shaft 210 and the aligned central lumen 240 of the flanged device 204 to treat the native mitral valve, as shown in FIG. 10.

Once the desired treatment has been completed, the auxiliary medical device 900 may be proximally retracted from the catheter-based system 200. As a distal tip of the auxiliary medical device 900 travels proximal of the sealing mechanism 260, the sealing mechanism 260 seals the central lumen 240 of the flanged device shaft 232. More precisely, the sealing mechanism 260 seals the central lumen 240 such that fluid will not flow through the central lumen 240 of the flanged device shaft 232.

Figure 11:
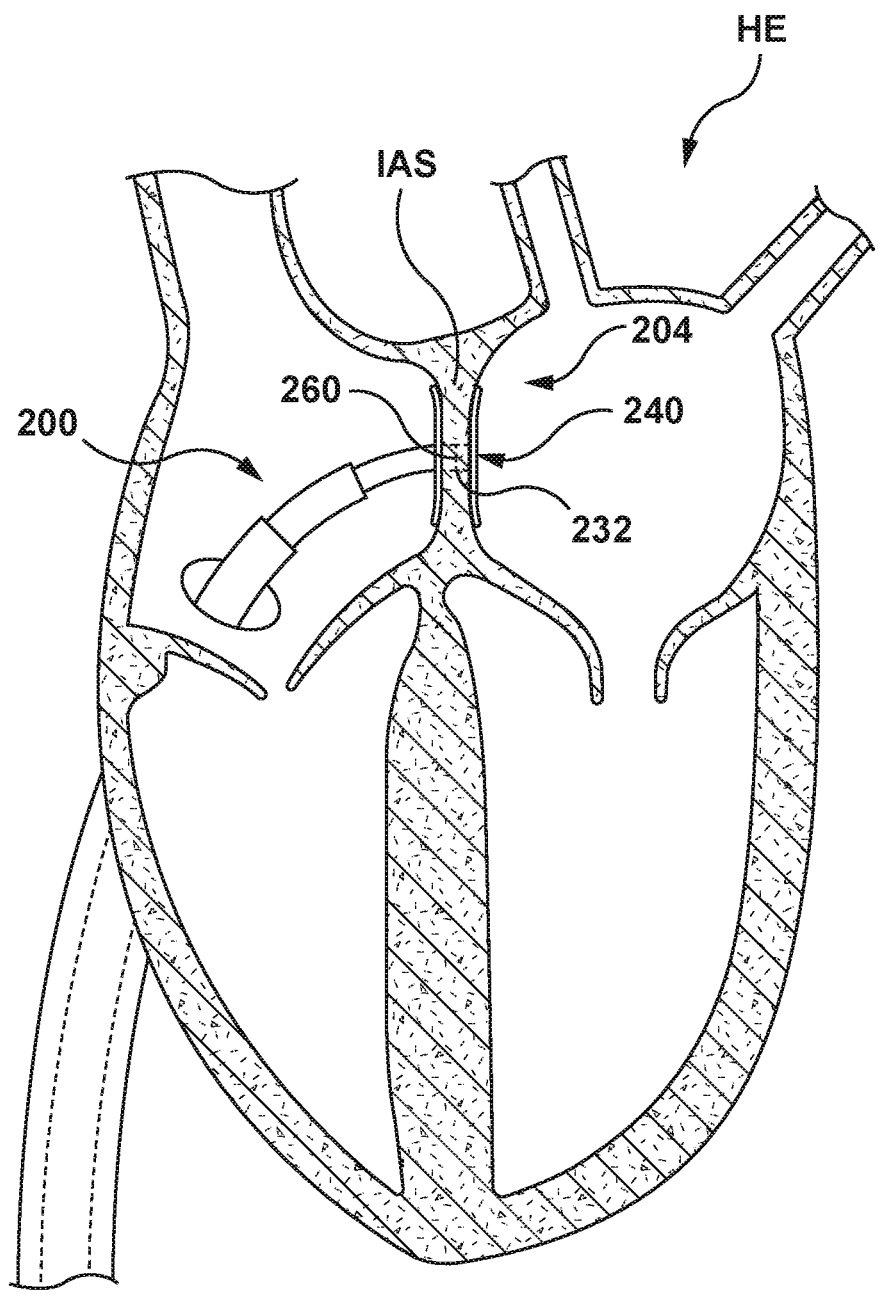
FIG. 11 is an illustration of the catheter-based system of FIG. 2A in situ, wherein the catheter-based system has been proximally retracted to manipulate or articulate the interatrial septum to the native shape.

With the auxiliary medical device 900 removed from the catheter-based system 200 and the sealing mechanism 260 sealing the central lumen 240 of the flanged device shaft 232, the catheter-based system 200 may be proximally retracted to manipulate or articulate the flanged device 204 and the interatrial septum IAS sandwiched there-between, as shown in FIG. 11.

Figure 12A:
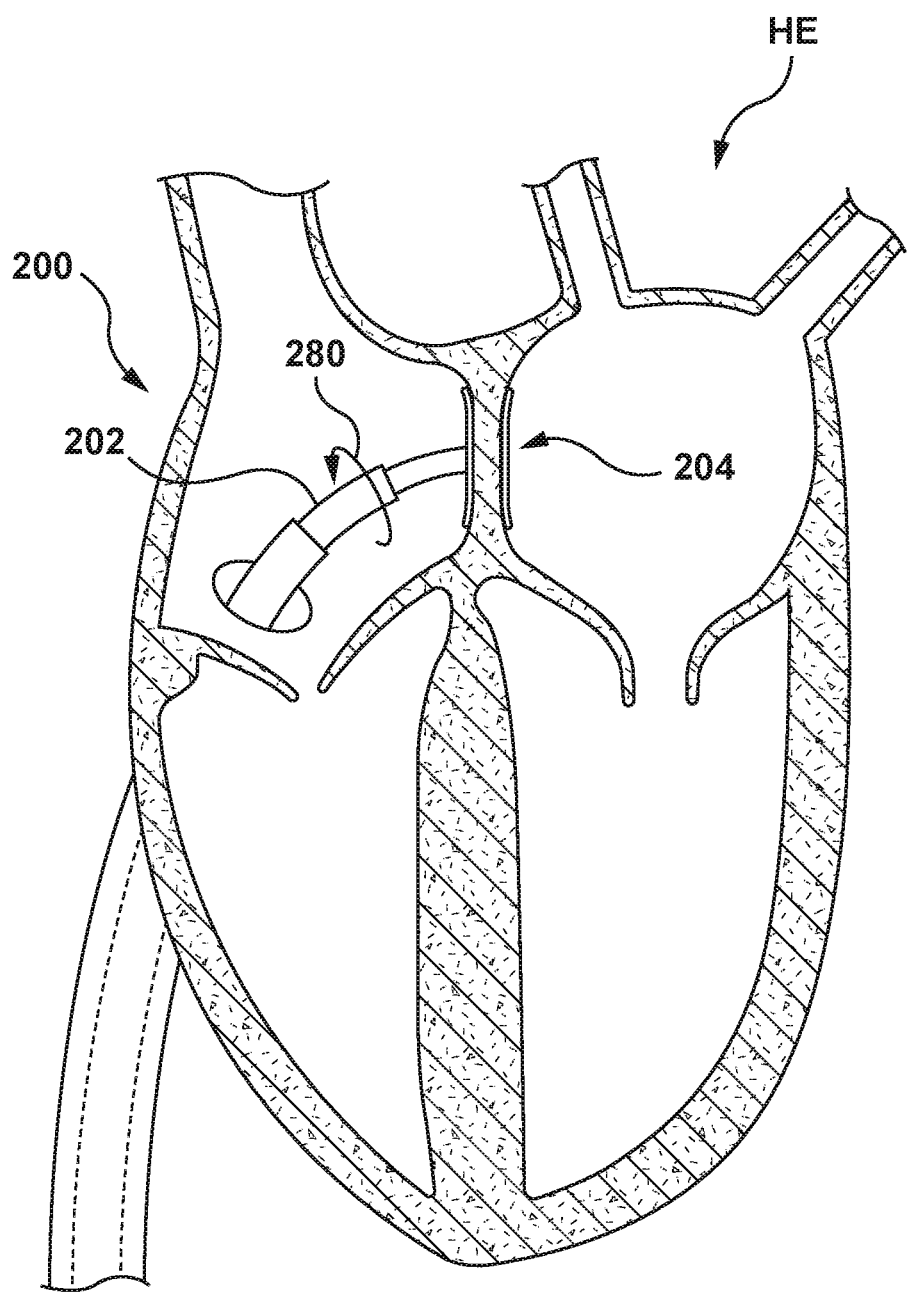
FIG. 12A is an illustration of the catheter-based system of FIG. 2A in situ, wherein a catheter has been rotated to uncouple the catheter from the flanged device.

In some embodiments, when the interatrial septum IAS has returned to its native shape and the central lumen 240 of the flanged device shaft 232 is sealed by the sealing mechanism 260, the catheter 202 is rotated, as shown in FIG. 12A, such that the plurality of threads 252 at the distal portion 248 of the inner shaft 210 disengage from the plurality of threads 254 of the flanged device 204 to uncouple the inner shaft 210 from the flanged device 204.

Figure 12B:
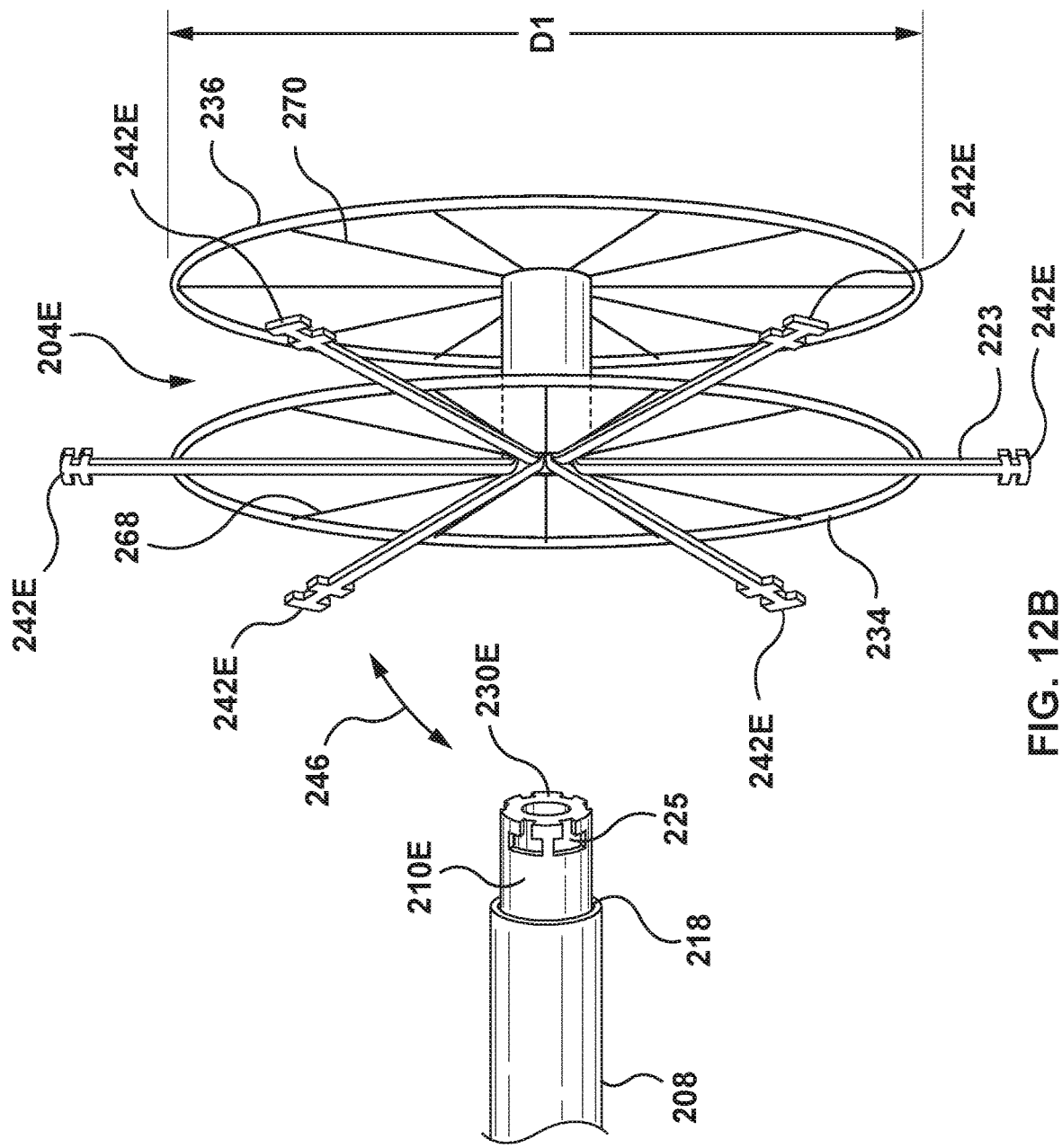
FIG. 12B is an illustration of a catheter-based system configured in accordance with an embodiment hereof, wherein a flanged device of FIGS. 3E-3H has been uncoupled from a catheter.

In some embodiments, wherein the flanged device 204E includes one or more coupling arms 223, when the interatrial septum IAS has returned to its native shape and the central lumen 240 of the flanged device shaft 232E is sealed by the sealing mechanism 260, the outer sheath 208 of the catheter 202 is proximally retracted to release the coupling arms 223 from the distal end 230E of the inner shaft 210E, as shown in FIG. 12B, such that the proximal ends 242E of the arms 223 disengage from the plurality of grooves 225 of the distal end 230E of the inner shaft 210E to uncouple the flanged device 204E from the inner shaft 210E.

In some embodiments, wherein the coupling mechanism 246 includes one or more sutures, when the interatrial septum IAS has returned to its native shape and the central lumen 240 of the flanged device shaft 232 is sealed by the sealing mechanism 260, tension within the sutures can be released and the sutures removed thus uncoupling the flanged device 204 from the inner shaft 210.

Figure 13:
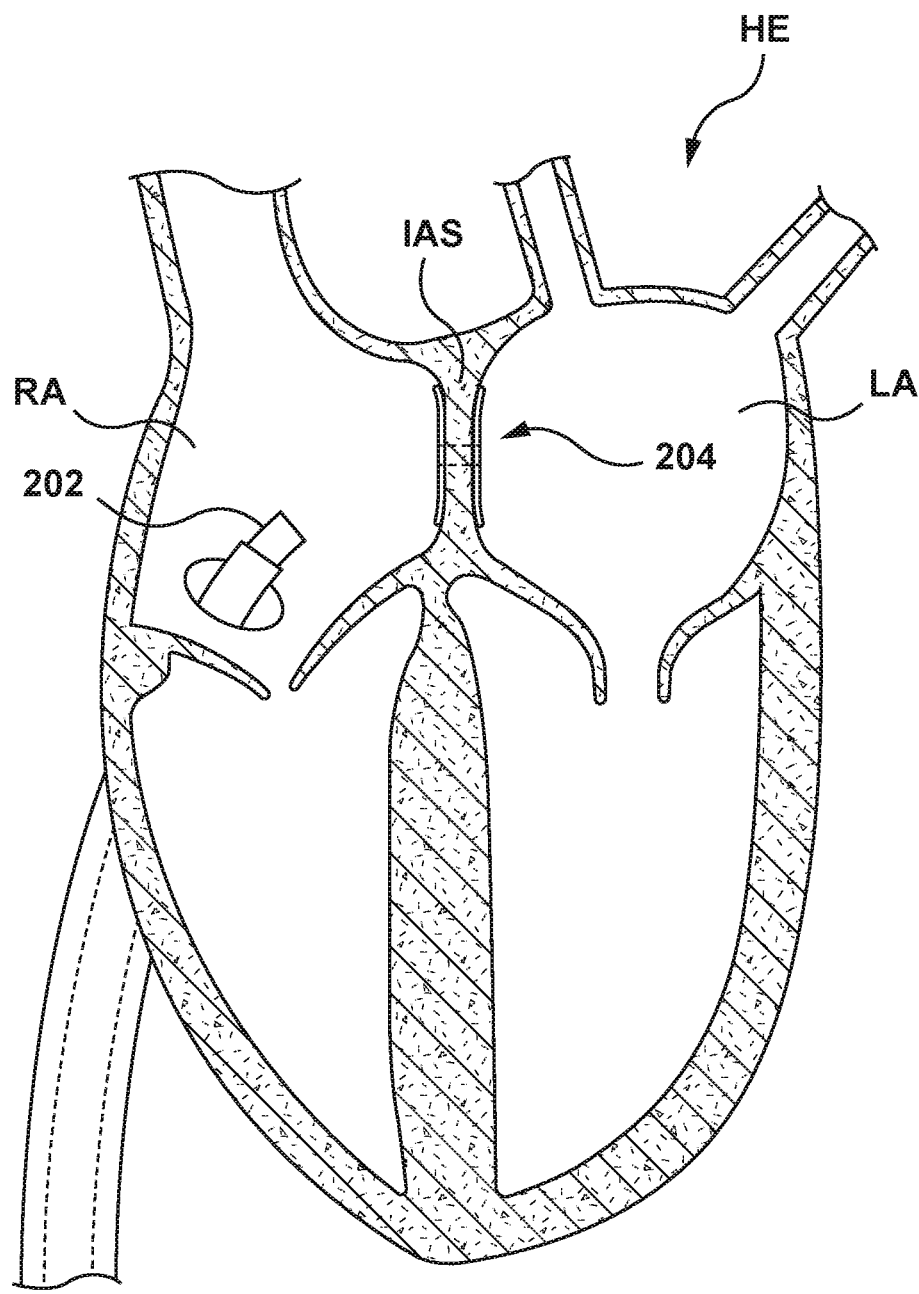
FIG. 13 is an illustration of the catheter-based system of FIG. 2A in situ, wherein the catheter has been proximally retracted to leave the flanged device at the transseptal puncture of the interatrial septum.

Once the coupling mechanism 246 has been actuated or manipulated to release or uncouple the flanged device 204 from the inner shaft 210, the catheter 202 is proximally retracted, as shown in FIG. 13. The flanged device 204 is configured to remain within the patient, as shown in FIG. 13. The proximal and distal anchors 234, 236 may include a biological or pharmacological substance for example, and not by way of limitation, to promote tissue ingrowth, to prevent infection, to prevent thrombosis, or other substances or combinations of substances suitable for the purposes described herein.

While the sealing mechanism 260 of the flanged device 204 is described as a hemostatic seal disposed within the central lumen 240 of the flanged device shaft 232, alternatively the central lumen 240 of the flanged device shaft 232 may be sealed by other sealing mechanisms such as, but not limited to flap mechanisms, iris mechanisms, or any other sealing mechanisms as appropriate. In some embodiments, the sealing mechanism 260 may be configured to seal permanently. Alternatively, the sealing mechanism 260 may be configured to allow future passage of one or more devices following the release of the flanged device 204 from the catheter 202.

FIGS. 4-13 are sectional cut-away views of a heart HE illustrating a transseptal approach for supporting and manipulating or articulating an interatrial septum IAS of the heart HE using the catheter-based system 200, for example one shown in FIGS. 2A-3H in accordance with embodiments hereof. With reference to FIG. 4, a guide catheter GC is shown having been introduced into the vasculature via a percutaneous entry point, such as with the Seldinger technique, and tracked through the vasculature and into a right atrium RA of the heart HE such that a distal end of the guide catheter GC is positioned within the right atrium RA. Intravascular access to the right atrium RA may be achieved via a percutaneous access site to femoral venous access up to the inferior venal cava, or other known access routes. Thereafter, a guidewire (not shown in FIGS. 4-13) is directed into the right atrium RA, traverses the right atrium RA and is made to puncture, with the aid of a transseptal needle or pre-existing hole, the interatrial septum IAS, thereby entering the left atrium LA. Once the guidewire (not shown in FIGS. 4-13) is positioned, the endoluminal entry port and the interatrial septum IAS are dilated to permit entry of the catheter-based system 200 into the left atrium LA. Although described as a transfemoral antegrade approach for percutaneously accessing the left atrium LA, the guide catheter GC may be positioned within the desired area of the heart HE via other different methods such as a transseptal antegrade approach via a thoracotomy.

Referring again to FIG. 4, and in a next deployment step, the clinician advances the catheter-based system 200 with the flanged device 204 in the radially collapsed configuration restrained within the outer sheath 208 of the catheter 202 through the guide catheter GC, through the puncture in the interatrial septum IAS, and into the left atrium LA using established percutaneous transcatheter procedures. The catheter-based system 200 is distally advanced until at least the distal anchor 236 of the flanged device 204 is disposed within the left atrium LA.

When the distal anchor 236 of the flanged device 204 is disposed within the left atrium LA, the outer sheath 208 is proximally retracted to expose the distal anchor 236, as shown in FIG. 5. More particularly, the outer sheath actuator mechanism 214 (not shown in FIGS. 4-13) of the handle 206 (not shown in FIGS. 4-13) of the catheter 202 is manipulated to proximally retract the outer sheath 208. When proximally retracted, the outer sheath 208 releases the distal anchor 236 and the distal anchor 236 self-expands, and transitions from the collapsed state to the expanded state within the left atrium LA, as shown in FIG. 6.

When the distal anchor 236 is in the expanded state within the left atrium LA, the catheter-based system 200 is proximally retracted to position the proximal surface 264 of the distal anchor 236 adjacent to and engaged with the interatrial septum IAS within the left atrium LA, as shown in FIG. 7.

Referring to FIG. 8, when the distal anchor 236 is engaged with the interatrial septum IAS within the left atrium LA, the outer sheath actuator mechanism 214 (not shown in FIGS. 4-13) of the handle 206 (not shown in FIGS. 4-13) is again manipulated to proximally retract the outer sheath 208 to release the proximal anchor 234 within the right atrium RA. When the proximal anchor 234 is released from the outer sheath 208, the proximal anchor 234 self-expands and transitions from the collapsed state to the expanded state within the right atrium RA. The distal surface 258 of the proximal anchor 234 engages the interatrial septum IAS within the right atrium RA such that the flanged device 204 is anchored to the interatrial septum IAS.

Once the flanged device 204 is in the radially expanded configuration and anchored to the interatrial septum IAS with the proximal and distal anchors 234, 236 of the flanged device 204 engaged with opposing sides of the interatrial septum IAS, the catheter-based system 200 is distally advanced and/or deflected to manipulate, articulate or move the interatrial septum IAS, deforming the interatrial septum IAS, as shown in FIG. 9. Manipulation or articulation of the flanged device 204 and the interatrial septum IAS reduces the angle A° between the first central axis CA1 extending through the transseptal puncture and the second central axis CA2 extending through the native mitral valve.

With reference to FIG. 10, when the interatrial septum IAS has been manipulated or articulated by the flanged device 204, an auxiliary medical device 900 may be advanced through the catheter-based system 200 to effect desired treatment on the native mitral valve MV. Once the treatment of the native mitral valve MV is complete, the auxiliary medical device 900 is retracted from the catheter-based system 200. As the auxiliary medical device is retracted proximal of the sealing mechanism 260 of the flanged device shaft 232, the central lumen 240 is sealed by the sealing mechanism 260.

Directing attention next to FIG. 11, when the central lumen 240 of the flanged device shaft 232 has been sealed by the sealing mechanism 260, the catheter-based system 200 is proximally retracted. The catheter-based system 200 is proximally retracted to return the interatrial septum IAS to the native shape.

In an embodiment, when the interatrial septum IAS is in the native shape, the handle 206 (not shown in FIGS. 4-13) of the catheter 202 is rotated in a direction of arrow 280, as shown in FIG. 12. The catheter 202 is rotated until the catheter 202 uncouples from the flanged device 204. In an alternative embodiment, when the interatrial septum IAS is in the native shape, the outer sheath actuation mechanism 214 (not shown in FIGS. 4-13) is again manipulated to proximally retract the outer sheath 208 to fully release or deploy the flanged device 204 from the catheter 202. In another alternative embodiment, when the interatrial septum IAS is in the native shape, one or more elongate tension members are removed (not shown in FIGS. 4-13) thus uncoupling the flanged device 204 from the catheter 202.

With reference to FIG. 13, once the coupling mechanism 246 has been actuated or manipulated to uncouple the flanged device 204 from the catheter 202, the catheter 202 is proximally retracted, leaving the fully deployed flanged device 204 disposed in the right and left atriums, and extending through the interatrial septum IAS.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery, positioning, and manipulation and/or articulation of the flanged device 204 and the interatrial septum IAS. In another embodiment, selected outer surfaces of the flanged device 204 may be treated to enhance the echogenicity of the flanged device 204. In some embodiments, image guidance components (e.g., IVUS, OCT) may be coupled to a distal segment of the catheter 202 to provide three-dimensional images of the vasculature/heart to facilitate positioning, orienting, and manipulation and/or articulation of the flanged device 204 and the interatrial septum IAS.

When the catheter 202 has been removed from the patient, the guide catheter GC may be removed using established percutaneous transcatheter procedures. The flanged device 204 remains in the radially expanded configuration at the interatrial septum IAS, sealing the transseptal puncture TSP.

FIGS. 14A-15C illustrate a catheter-based system 300 according to another embodiment hereof. The catheter-based system 300 includes a catheter 302 and a flanged device 304. The catheter-based system 300 is configured to percutaneously support and manipulate or articulate an interatrial septum of a heart according to an embodiment of the present invention. In the embodiment of FIGS. 14A-15C, a proximal anchor of the flanged device 304 is a proximal anchor balloon 350 and a distal anchor of the flanged device 304 is a distal anchor balloon 342.

Figure 14A:
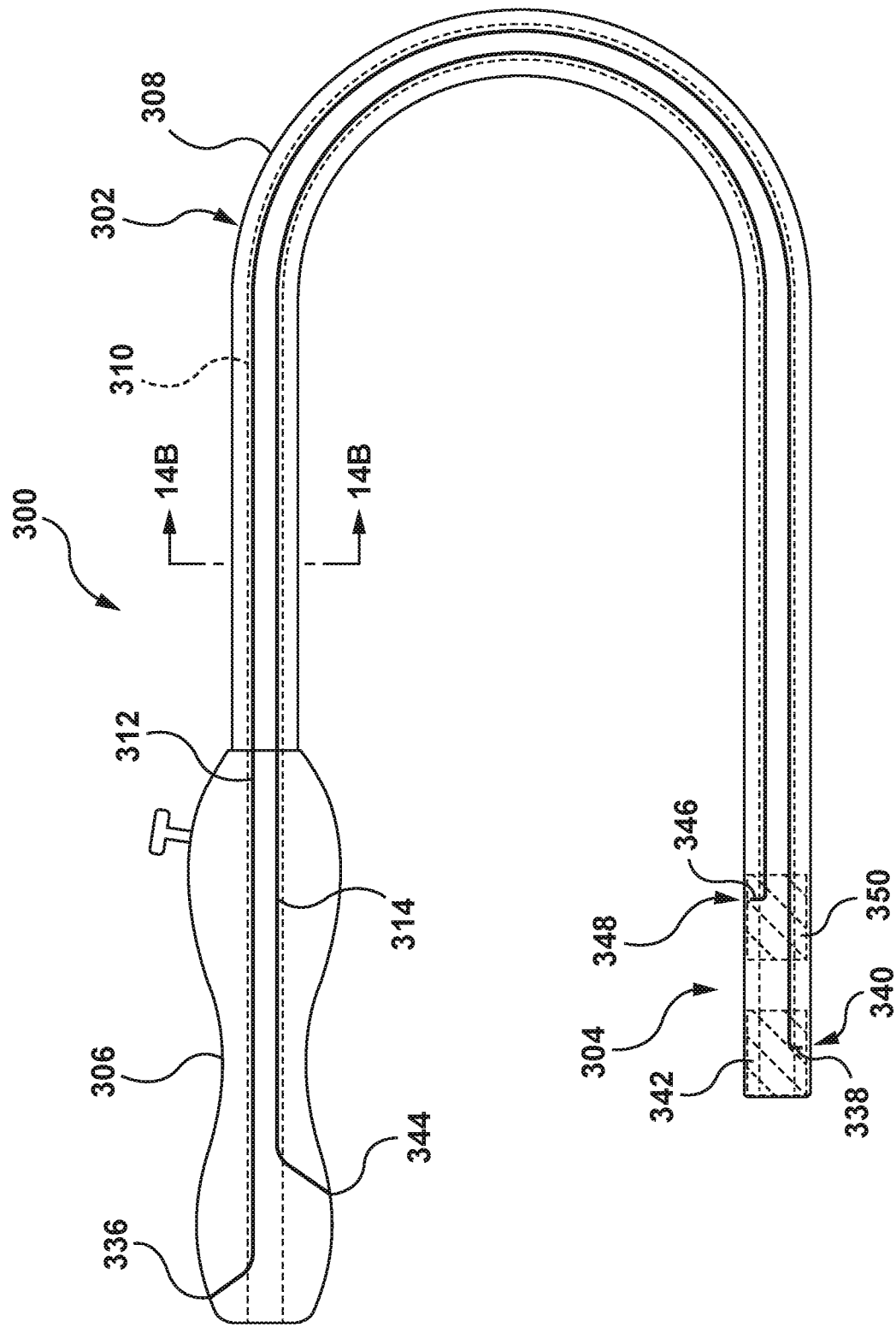
FIG. 14A is a side view illustration of a catheter-based system configured in accordance with another embodiment hereof, wherein the flanged device is mounted at a distal portion thereof and the flanged device is shown in a radially collapsed configuration for delivery.
Figure 14B:
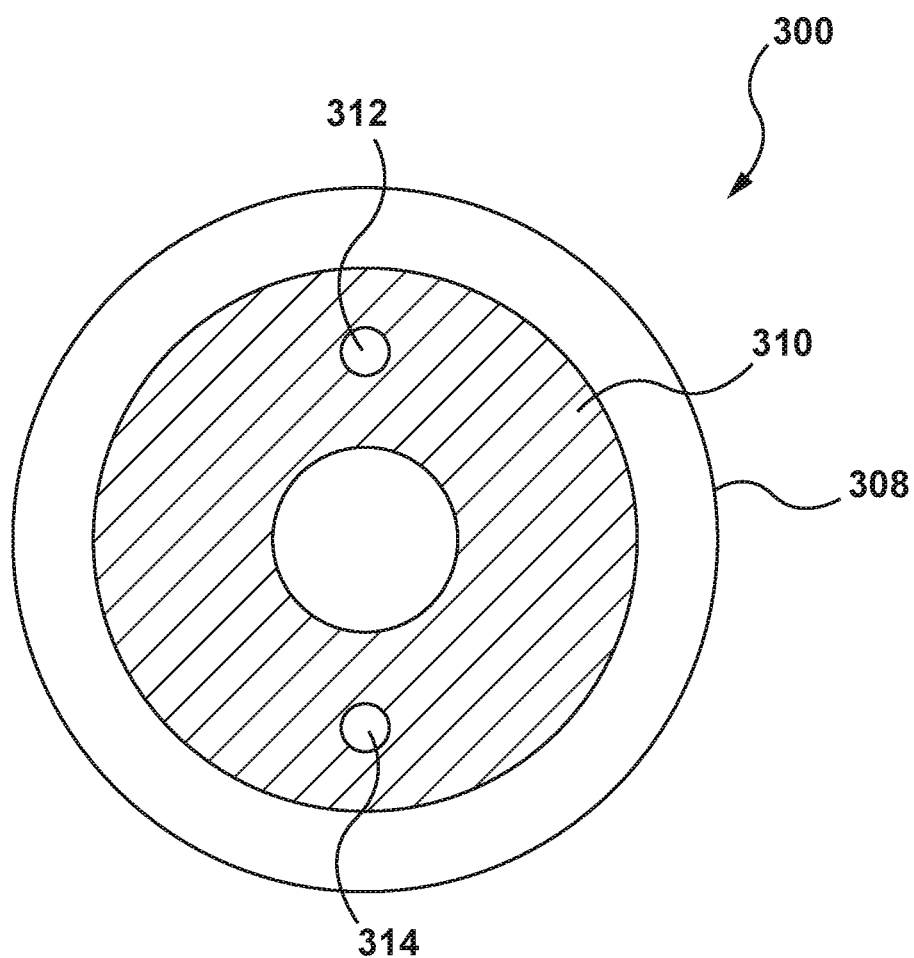
FIG. 14B is a cross-sectional illustration of the catheter-based system of FIG. 14A, taken at line 14B-14B of FIG. 14A.

Referring to the illustrations of FIGS. 14A and 14B, the catheter 302 includes a handle 306, and outer sheath 308, an inner shaft 310, a first inflation lumen 312, and a second inflation lumen 314, as shown in FIG. 14A. The catheter 302 is configured to deliver, deploy, and manipulate or articulate the flanged device 304 across a transseptal puncture of the interatrial septum of the heart. The handle 306, the outer sheath 308, and the inner shaft 310 are similar to the handle 206, the outer sheath 208, and the inner shaft 210 described previously. Therefore similar construction and alternative details will not be repeated. However, with the catheter 302 of FIGS. 14A and 14B, the inner shaft 310 includes the first and the second inflation lumen 312, 314 for transitioning the flanged device 304 between radially collapsed and radially expanded configurations. While the catheter 302 is shown as including the outer sheath 308 operably coupled to the handle 306, this is by way of example and not limitation, and it will be understood that in embodiments hereof the outer sheath 308 is optional and may be omitted.

The first inflation lumen 312 extends through the inner shaft 310, as shown in FIG. 14A, and in an embodiment may be defined by the inner shaft 310, as shown in the cross-sectional view of the catheter 302 in FIG. 14B. The first inflation lumen 312 includes a proximal end 336 and a distal end 338 in fluid communication with a distal anchor balloon inflation port 340, as shown in FIG. 14A. The distal anchor balloon inflation port 340 is in fluid communication with an interior of the distal anchor balloon 342 of the flanged device 304.

The second inflation lumen 314 also extends through, and may be defined by, the inner shaft 310, as shown in FIG. 14A and the cross-sectional view of the catheter 302 of FIG. 14B. The second inflation lumen 314 includes a proximal end 344 and a distal end 346 in fluid communication with a proximal anchor balloon inflation port 348. The proximal anchor balloon inflation port 348 is in fluid communication with an interior of the proximal anchor balloon 350 of the flanged device 304.

In the embodiment shown, the first inflation lumen 312 and the second inflation lumen 314 are configured such that the distal anchor balloon 342 and the proximal anchor balloon 350 of the flanged device 304 inflate/deflate independent of each other. The proximal ends 336, 344 of the first and second inflation lumen 312, 314, respectively, allow inflation fluid received through inflation ports (not shown in FIGS. 14A and 14B) of the handle 306 to be delivered to the distal and proximal anchor balloons 342, 350 respectively. The handle 306 provides a luer hub or other type of fitting that may be connected to a source of inflation fluid and may be of another constructional configuration without departing from the scope of the present invention. The tool catheter 302 may have alternate configurations known to one skilled in the art. Moreover, while described herein with a first and a second inflation lumen 312, 314, this is by way of example and not limitation and in another embodiment the catheter 302 may include only one inflation lumen in fluid communication with both the proximal and the distal anchor balloons 350, 342.

Figure 15B:
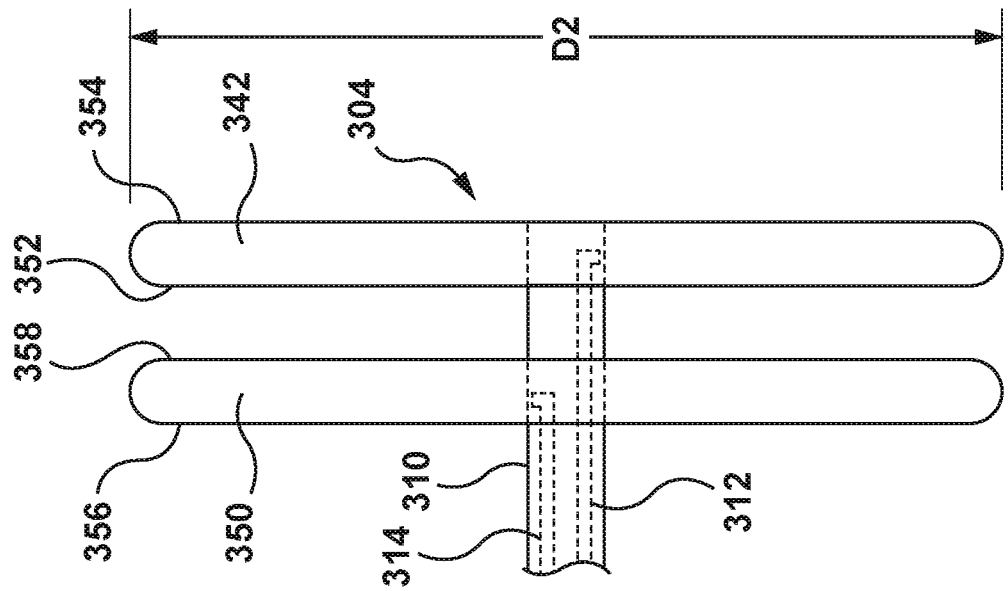
FIG. 15B is a side view illustration of the flanged device of FIG. 15A, wherein the flanged device is in a radially expanded configuration.
Figure 15A:
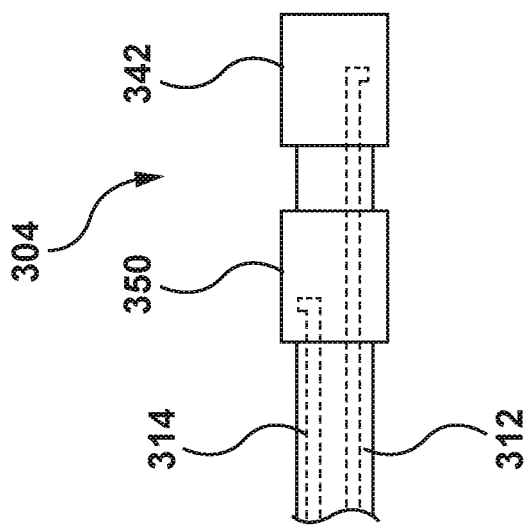
FIG. 15A is a perspective illustration of the flanged device of the catheter-based system of FIG. 14A configured in accordance with an embodiment hereof, wherein the flanged device is in the radially collapsed configuration.

FIGS. 15A-15C illustrate the flanged device 304 according to an embodiment hereof. The flanged device 304 includes the proximal anchor balloon 350 and the distal anchor balloon 342. The flanged device 304 includes a radially collapsed configuration for delivery to an interatrial septum of a heart, wherein the proximal anchor balloon 350 and the distal anchor balloon 342 are each in a collapsed state, as shown in FIG. 15A. The flanged device 304 further includes a radially expanded configuration for supporting and articulating the interatrial septum about a transseptal puncture, wherein the proximal anchor balloon 350 and the distal anchor balloon 342 are each in an expanded state, as shown in FIGS. 15B and 15C. More precisely, when the flanged device 304 is in the radially expanded configuration, the distal anchor balloon 342 is adjacent to and engaged with the interatrial septum in the left atrium and the proximal anchor balloon 350 is adjacent to and engaged with the interatrial septum in the right atrium. Thus, when the flanged device 304 is in the radially expanded configuration, the interatrial septum IAS is disposed between the proximal anchor balloon 350 and the distal anchor balloon 342 and the flanged device 304 provides support to, and the ability to manipulate or articulate the interatrial septum.

The distal anchor balloon 342 is coupled to the inner shaft 310 and includes a proximal surface 352 and a distal surface 354, as shown in FIG. 15B. The distal anchor balloon 342 is disposed at a distal portion of the inner shaft 310 and spaced from, the proximal anchor balloon 350. The distal anchor balloon 342 has a collapsed state wherein the distal anchor balloon 342 is not inflated, as shown in FIG. 15A. The distal anchor balloon 342 has an expanded state, wherein the distal anchor balloon 342 is inflated via inflation fluid delivered through the first inflation lumen 312 (as shown in phantom in FIGS. 15A and 15B) to the interior of the distal anchor balloon 342. When in the expanded state, the distal anchor balloon 342 radially expands to a general disc or flat cylindrical shape, as shown in FIGS. 15B and 15C. The proximal surface 352 of the distal anchor balloon 342 is configured to engage a wall/surface of the interatrial septum within the left atrium when the distal anchor balloon 342 is in the expanded state and the flanged device 304 is disposed at a transseptal puncture in the interatrial septum. The distal anchor balloon 342 in the expanded state and engaged with the interatrial septum in the left atrium is further configured to support the interatrial septum and to transmit forces applied to the distal anchor balloon 342 across a large surface area of the interatrial septum engaged with the proximal surface 352 of the distal anchor balloon 342. The distal anchor balloon 342 is of a suitable diameter D2 such that forces applied to the distal anchor balloon 342 may be distributed over a large surface area of the adjacent interatrial septum such that the interatrial septum is not damaged during articulation. In a non-limiting example, the diameter D2 of the distal anchor balloon 342 may be from 10 mm up to 30 mm. The distal anchor balloon 342 may be a non-compliant or semi-compliant balloon constructed of any suitable material such as, but not limited to polyethylene terephthalate (PET), nylon, or polyurethane.

The proximal anchor balloon 350 is coupled to the inner shaft 310 and includes a proximal surface 356 and a distal surface 358, as shown in FIG. 15B. The proximal anchor balloon 350 is disposed proximal of, and spaced from, the distal anchor balloon 342. The proximal anchor balloon 350 has a collapsed state wherein the proximal anchor balloon 350 is not inflated, as shown in FIG. 15A. The proximal anchor balloon 350 further has an expanded state, wherein the proximal anchor balloon 350 is inflated via inflation fluid delivered through the second inflation lumen 314 (shown in phantom in FIGS. 15A and 15B) to the interior of the proximal anchor balloon 350. When in the expanded state, the proximal anchor balloon 350 radially expands to a general disc or flat cylindrical shape, as shown in FIG. 15C. The distal surface 358 of the proximal anchor balloon 350 is configured to engage a wall/surface of the interatrial septum within the right atrium when the proximal anchor balloon 350 is in the expanded state and the flanged device 304 is disposed at a transseptal puncture in the interatrial septum. The proximal anchor balloon 350 in the expanded state and engaged with the interatrial septum in the right atrium is further configured to support the interatrial septum and to transmit forces applied to the proximal anchor balloon 350 across a large surface area of the interatrial septum engaged with the distal surface 358 of the proximal anchor balloon 350. The proximal anchor balloon 350 is of a suitable diameter D2 such that forces applied to the proximal anchor balloon 350 may be distributed over a large surface area of the adjacent interatrial septum such that the interatrial septum is not damaged during articulation. Similar to the distal anchor balloon 342, in a non-limiting example, the diameter D2 of the proximal anchor balloon 350 may be from 10 mm up to 30 mm. The proximal anchor balloon 350 may be a non-compliant or semi-compliant balloon constructed of any suitable material such as, but not limited to polyethylene terephthalate (PET), nylon, or polyurethane.

Figure 16:
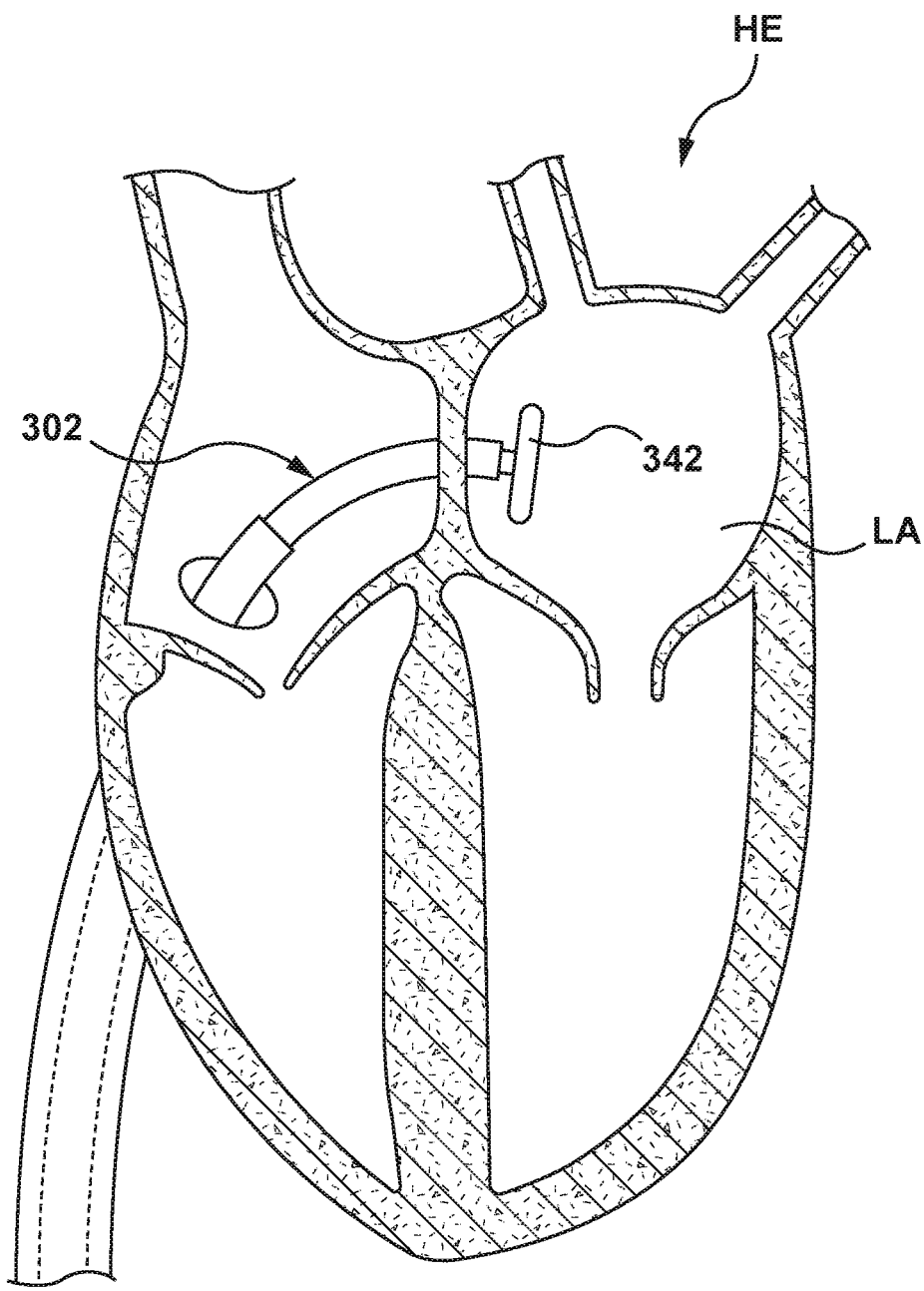
FIG. 16 is an illustration of the catheter-based system of FIG. 14A in situ, wherein an outer sheath of a catheter has been proximally retracted to release a distal anchor balloon, and the distal anchor balloon has been inflated to an expanded state.
Figure 18:
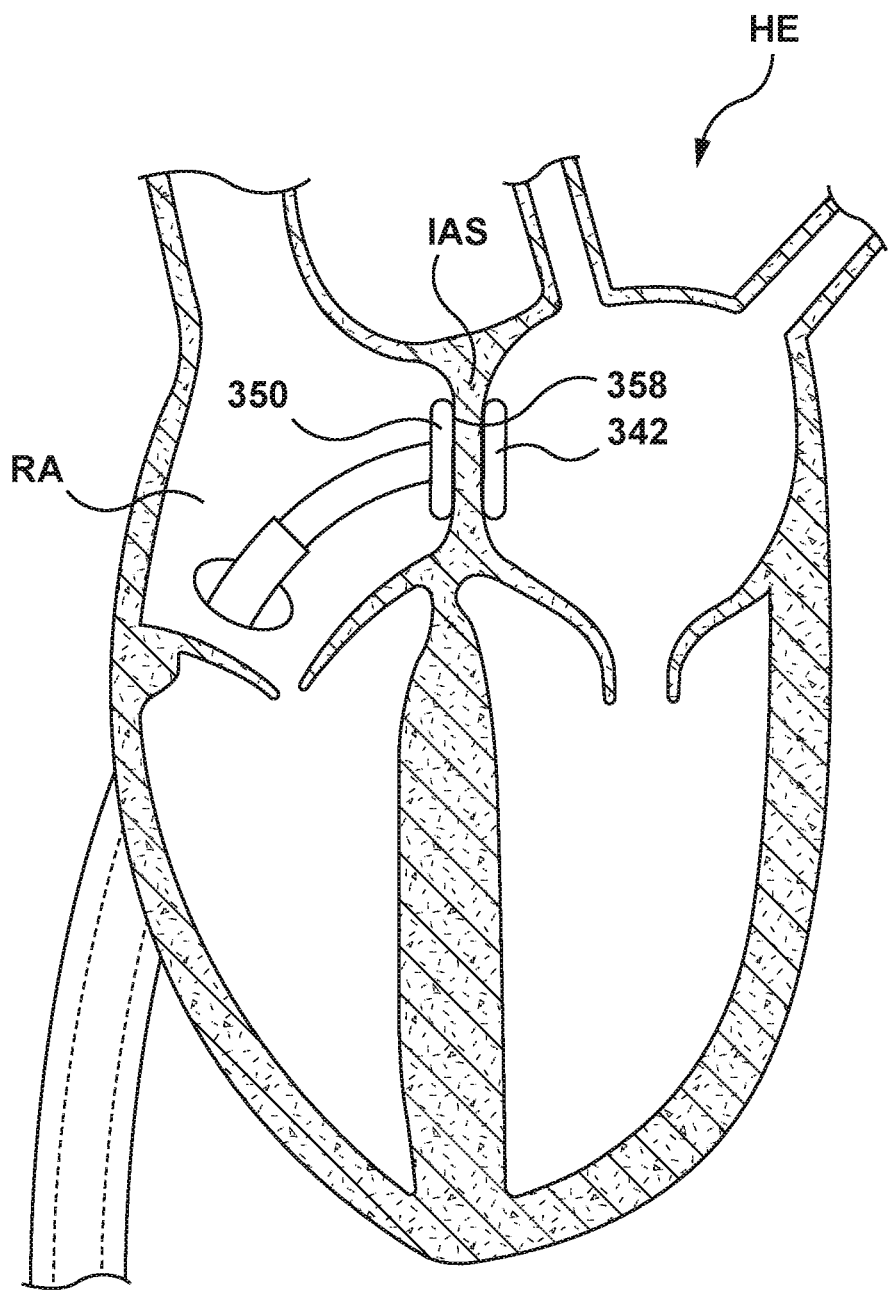
FIG. 18 is an illustration of the catheter-based system of FIG. 14A in situ, wherein the outer sheath of the catheter has been proximally retracted to release a proximal anchor balloon, and the proximal anchor balloon has been inflated to an expanded state adjacent the interatrial septum within the right atrium.

The interaction of the components of the catheter-based system 300 to deliver and manipulate or articulate the flanged device 304 and to further support and manipulate or articulate the interatrial septum of a heart are similar to the interaction of the components of the catheter-based system 200 described previously. However, with the catheter-based system 300, the distal anchor balloon 342 and the proximal anchor balloon 350 are each inflated to the expanded state. More specifically, when the distal anchor balloon 342 is disposed within the left atrium, inflation fluid under pressure is pumped thorough the first inflation lumen 312, through the distal anchor balloon inflation port 340 and into the interior of the distal anchor balloon 342 to transition the distal anchor balloon 342 from the collapsed state to the expanded state, as shown in FIG. 16. Similarly, when the proximal anchor balloon 350 is disposed within the right atrium, inflation fluid under pressure is pumped thorough the second inflation lumen 314, through the proximal anchor balloon inflation port 348 and into the interior of the proximal anchor balloon 350 to transition the proximal anchor balloon 350 from the collapsed state to the expanded state, as shown in FIG. 18.

Further, when the desired treatment has been effected and an auxiliary medical device 900 (not shown in FIGS. 14A-22) has been proximally retracted from the catheter-based system 300, inflation fluid may be withdrawn from the anchor balloons 342, 350 to deflate the anchor balloons 342, 350. In an embodiment, release of inflation fluid pressure permits inflation fluid to flow out of the distal and the proximal anchor balloons 342, 350 through the respective first and second inflation lumen 312, 314 such that the distal and the proximal anchor balloons 342, 350 transition from the expanded state to the collapsed state. Accordingly, the flanged device 304 transitions from the radially expanded configuration to the radially collapsed configuration, as shown in FIG. 21. The catheter-based system 300 may then be retracted to remove the catheter-based system 300 from the patient. A septal occluder device may be utilized to seal the transseptal puncture in the interatrial septum.

FIGS. 16-22 show schematically an embodiment of a method of delivering, and articulating the flanged device 304 and further supporting and articulating an interatrial septum IAS of a heart HE with the catheter-based system 300 of the present disclosure. The catheter-based system 300 and the flanged device 304 are similar to the catheter-based system 200 and the flanged device 204 described previously. However, in the embodiment of FIGS. 16-22, the flanged device 304, and more precisely the distal anchor balloon 342 and the proximal anchor balloon 350 must be inflated to transition to the expanded state. Therefore, details of the method up to the step of tracking and positioning the catheter-based system within the left atrium will not be repeated.

Referring next to FIG. 16, when the distal anchor balloon 342 is positioned within the left atrium, inflation fluid under pressure is pumped into the first inflation lumen 312 (not shown in FIGS. 16-22) to transition the distal anchor balloon 342 from the collapsed state to the expanded state within the left atrium LA. If the catheter-based system 300 includes the optional outer sheath 308 (not shown in FIGS. 16-22), prior to inflation of the distal anchor balloon 342, the outer sheath actuator mechanism 318 (not shown in FIGS. 16-22) of the handle 306 (not shown in FIGS. 16-22) is manipulated to proximally retract the outer sheath 308 (not shown in FIGS. 16-22) to release the distal anchor balloon 342.

Figure 17:
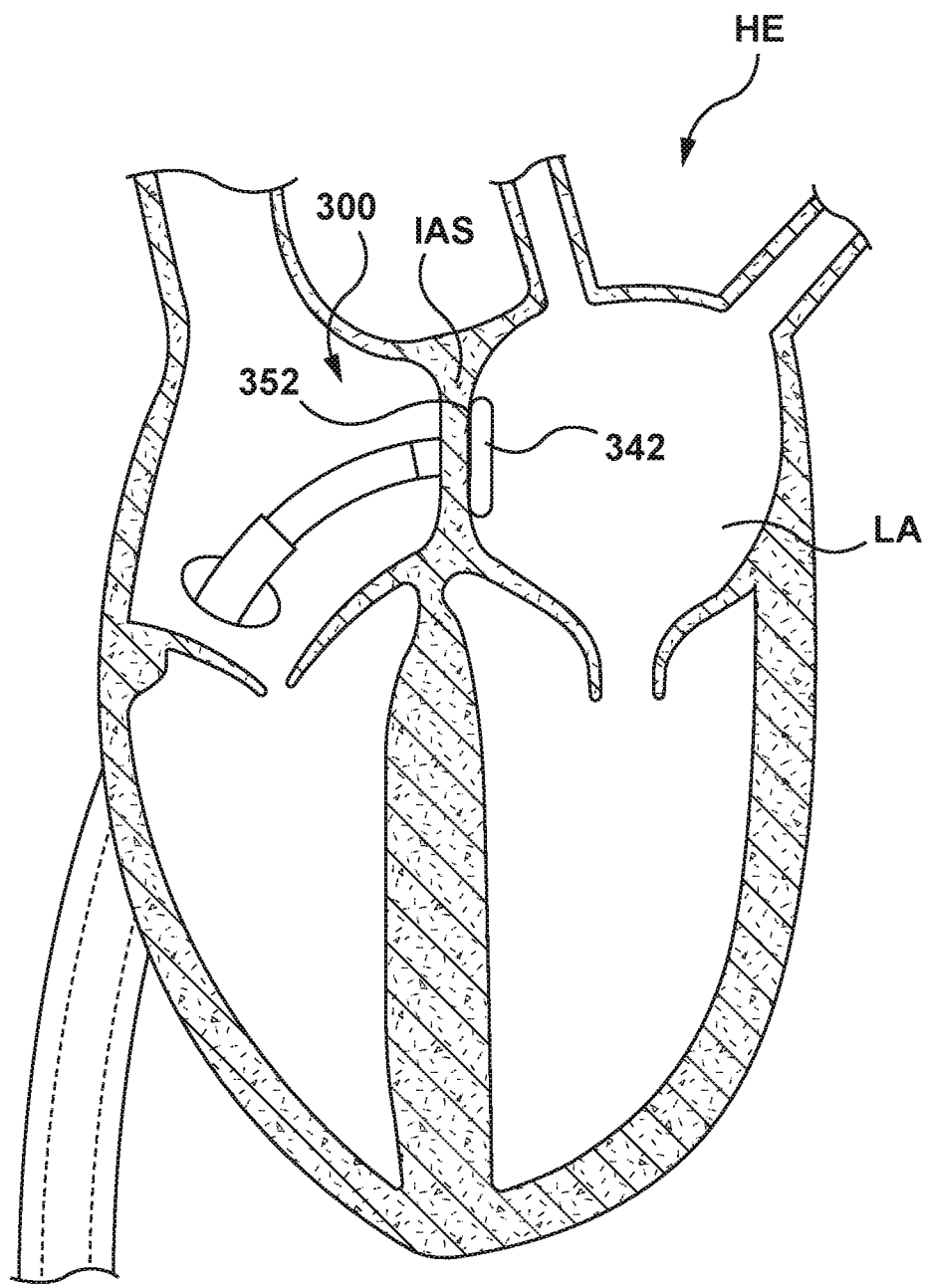
FIG. 17 is an illustration of the catheter-based system of FIG. 14A in situ, wherein the catheter-based system has been proximally retracted to position the distal anchor balloon adjacent the interatrial septum within the left atrium.

When the distal anchor balloon 342 is in the expanded state within the left atrium LA of the heart HE, the catheter-based system 300 is proximally retracted to position the proximal surface 352 of the distal anchor balloon 342 adjacent to and engaged with the interatrial septum IAS within the left atrium LA, as shown in FIG. 17.

Referring to FIGS. 17 and 18, when the distal anchor balloon 342 is engaged with the interatrial septum IAS in the left atrium LA and the proximal anchor balloon 350 is disposed within the right atrium RA, inflation fluid under pressure is pumped into the second inflation lumen 314 (not shown in FIGS. 16-22) to transition the proximal anchor balloon 350 from the collapsed state to the expanded state within the right atrium RA. When the proximal anchor balloon 350 transitions from the collapsed state to the expanded state, the distal surface 358 of the proximal anchor balloon 350, adjacent the interatrial septum IAS, engages the interatrial septum IAS within the right atrium RA. If the catheter-based system 300 includes the optional outer sheath 308 (not shown in FIGS. 16-22), prior to inflating the proximal anchor balloon 350, the outer sheath actuator mechanism 318 (not shown in FIGS. 16-22) of the handle 306 (not shown in FIGS. 16-22) is again manipulated to further proximally retract the outer sheath 308 (not shown in FIGS. 16-22) to release the proximal anchor balloon 350 within the right atrium RA.

Figure 19:
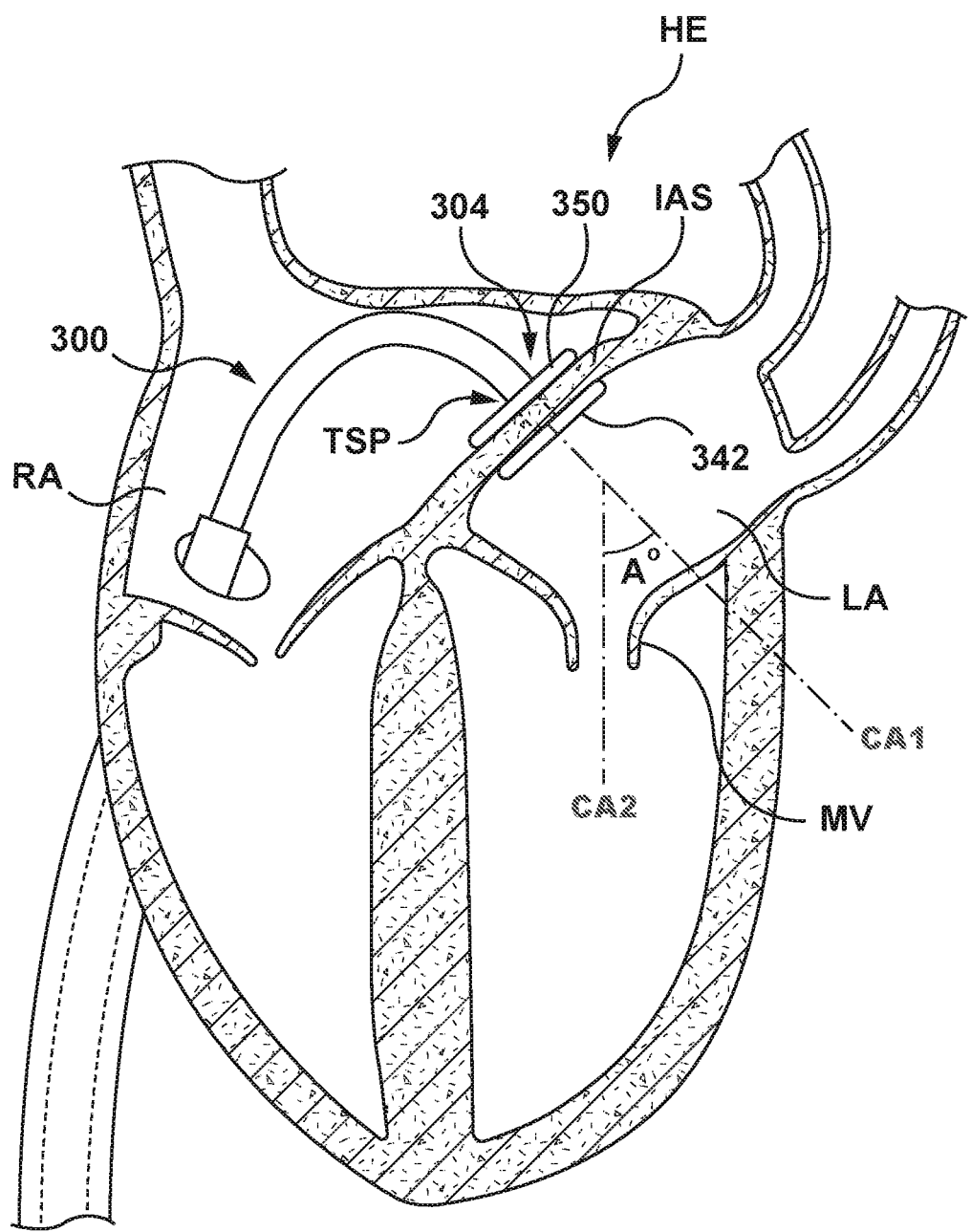
FIG. 19 is an illustration of the catheter-based system of FIG. 14A in situ, wherein the catheter-based system has been distally advanced to manipulate or articulate the interatrial septum to better align an axis of a transseptal puncture of the interatrial septum with a native mitral valve.

With the flanged device 304 in the radially expanded configuration, and the proximal anchor balloon 350 engaged with the interatrial septum IAS in the right atrium RA and the distal anchor balloon 342 engaged with the interatrial septum IAS in the left atrium LA, the catheter-based system 300 is distally advanced and/or deflected, if the catheter-based system 330 includes a deflection mechanism, to manipulate or articulate the interatrial septum IAS. More specifically, the catheter-based system 300 is distally advanced and/or deflected such that the flanged device 304, supporting the interatrial septum IAS, manipulates or articulates the interatrial septum, thereby deforming the interatrial septum IAS, as shown in FIG. 19. The catheter-based system 300 is distally advanced to decrease the angle A° between the first central axis CA1 extending through the transseptal puncture and the second central axis CA2 extending through the native mitral valve from an angle A° (as shown in FIG. 1) when the interatrial septum is not manipulated or articulated.

When the interatrial septum IAS has been manipulated or articulated by the flanged device 304, an auxiliary medical device may be advanced through the catheter-based system 300 to effect desired treatment on the native mitral valve MV. When the treatment of the native mitral valve MV is complete, the auxiliary medical device is retracted from the catheter-based system 300.

Figure 20:
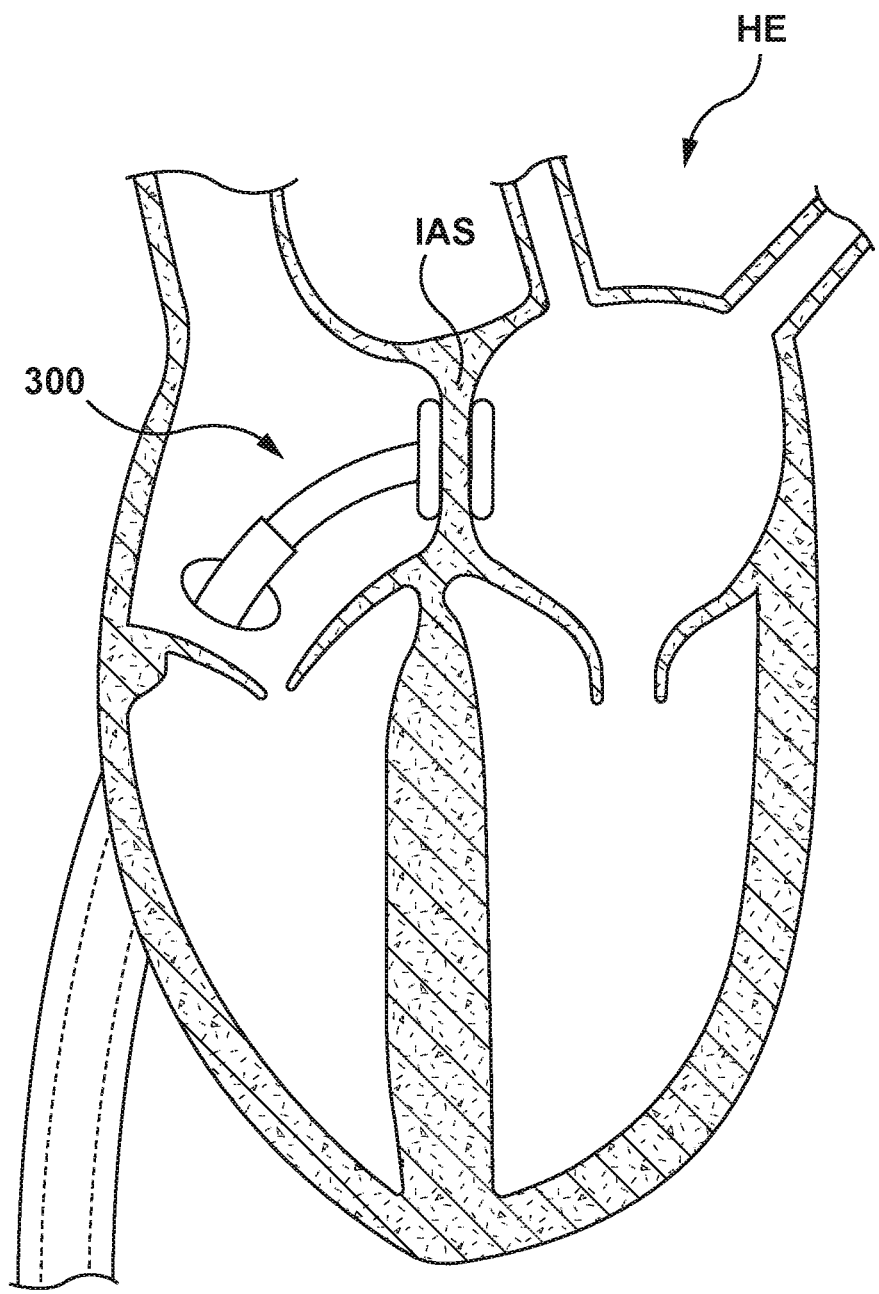
FIG. 20 is an illustration of the catheter-based system of FIG. 14A in situ, wherein the catheter-based system has been proximally retracted to manipulate or articulate the interatrial septum to the native shape.
Figure 21:
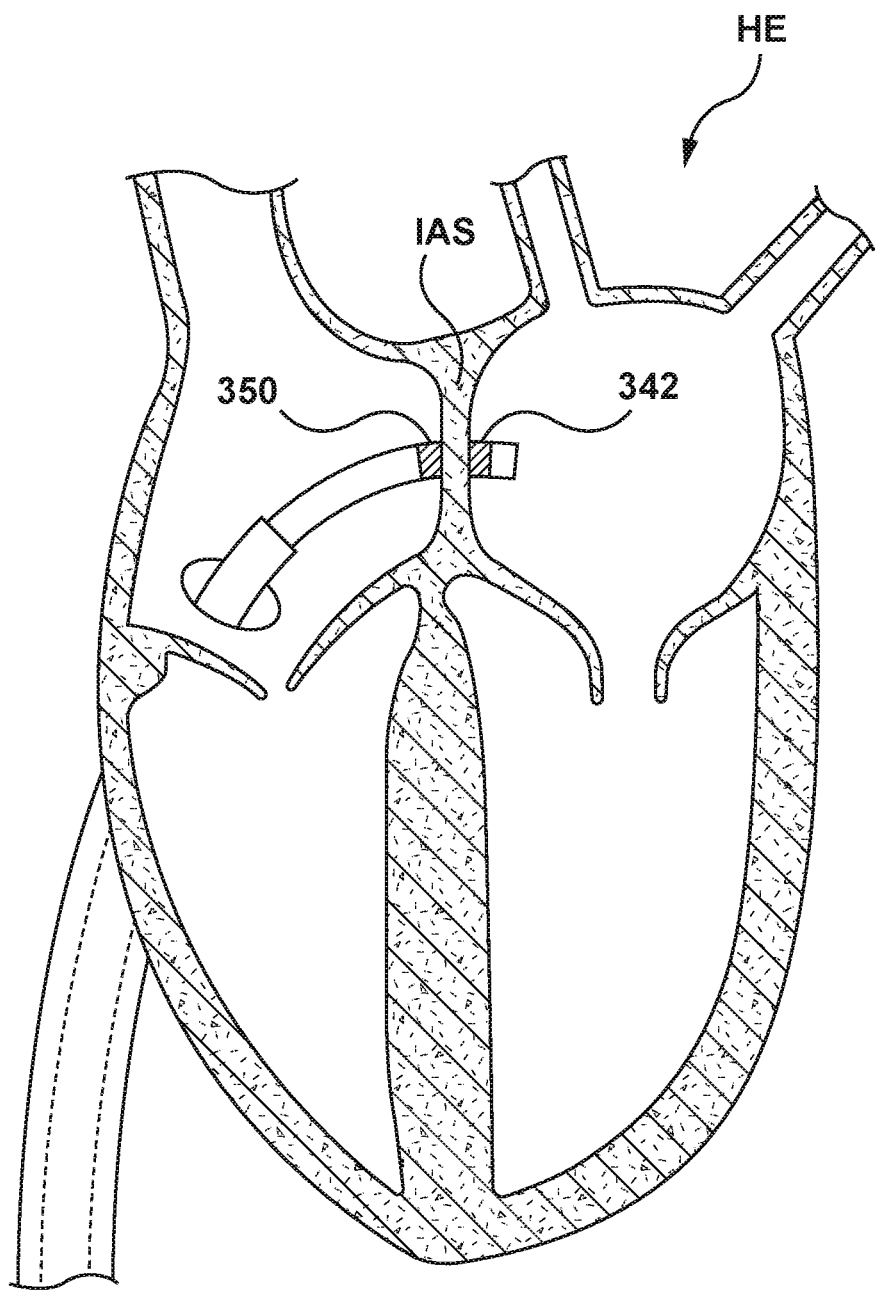
FIG. 21 is an illustration of the catheter-based system of FIG. 14A in situ, wherein the distal anchor balloon and the proximal anchor balloon have each been deflated flanged device.

When the auxiliary medical device has been removed from the catheter-based system 300, the catheter-based system 300 is proximally retracted to return the interatrial septum IAS to the native shape or orientation, as shown in FIG. 20.

Referring to FIG. 21, when the interatrial septum IAS has returned to the native shape or orientation, the inflation fluid pressure is removed from the first and the second inflation lumen 312, 314 (not shown in FIGS. 16-22), to transition the distal and proximal anchor balloons 342, 350 each to the collapsed state. In an embodiment, a vacuum is placed on the first and second inflation lumen 312, 314 to retain the distal and proximal anchor balloons 342, 350 each in the collapsed state. In embodiments with an outer sheath 308 (not shown in FIGS. 16-22), when the proximal and the distal anchor balloons 350, 342 are each in the collapsed state, the outer sheath 308 is distally advanced to encapsulate the uninflated proximal and distal anchor balloons 350, 342.

Figure 22:
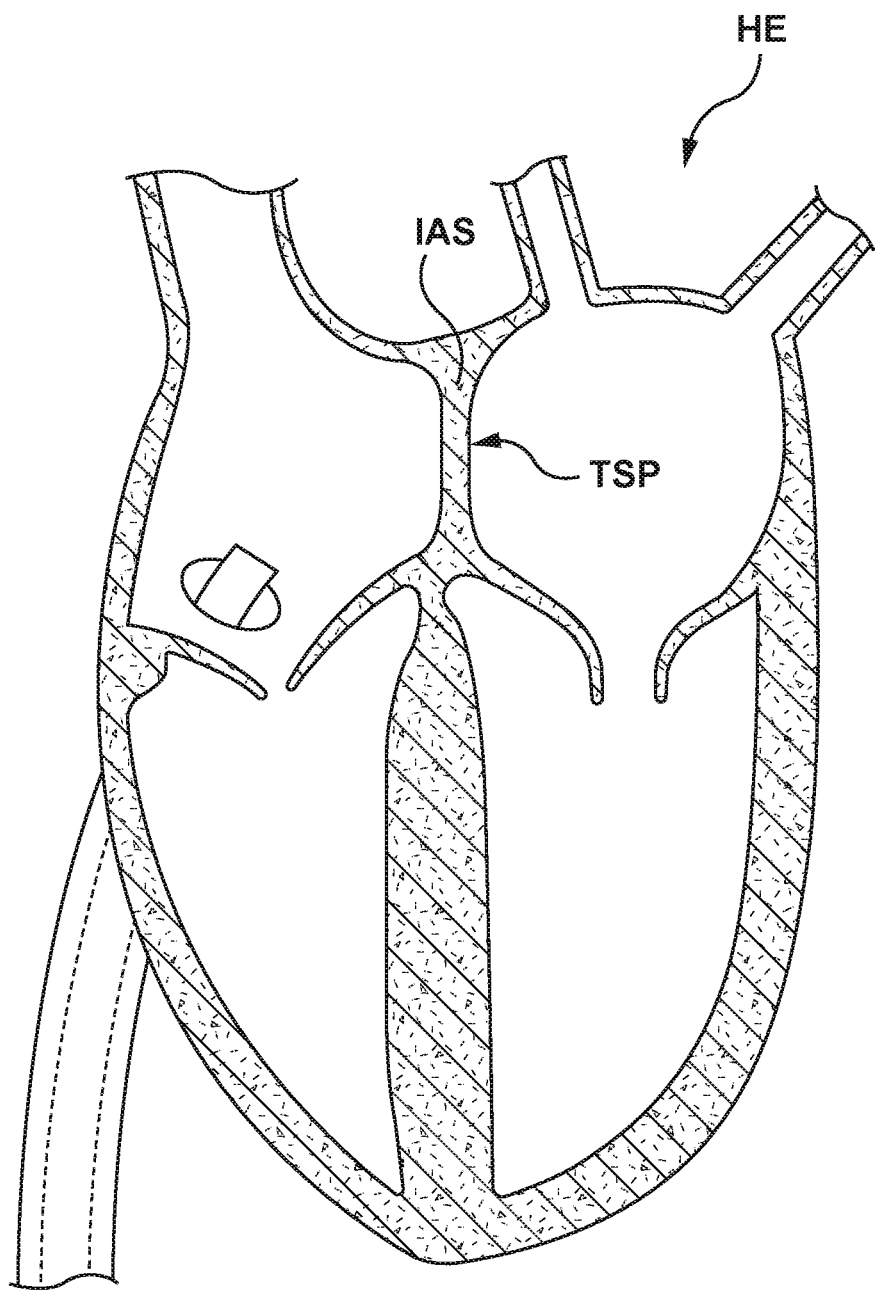
FIG. 22 is an illustration of the catheter-based system of FIG. 14A in situ, wherein the catheter-based system has been proximally retracted.

The catheter-based system 300 with the flanged device 304 may then be proximally retracted to remove them from the patient using established percutaneous transcatheter procedures, as shown in FIG. 22. With the flanged device 304 removed from the patient, the transseptal puncture TSP in the interatrial septum IAS may be sealed by known methods.

Image guidance, e.g., intracardiac echocardiography (ICE), fluoroscopy, computed tomography (CT), intravascular ultrasound (IVUS), optical coherence tomography (OCT), or another suitable guidance modality, or combination thereof, may be used to aid the clinician's delivery, positioning, and manipulation and/or articulation of the flanged device 304 and the interatrial septum IAS. In another embodiment, selected outer surfaces of the flanged device 304 may be treated such that the echogenicity of the flanged device 304 is enhanced. In some embodiments, image guidance components (e.g., IVUS, OCT) may be coupled to a distal segment of the catheter 302 to provide three-dimensional images of the vasculature to facilitate positioning, orienting, and manipulation and/or articulation of the flanged device 304 and the interatrial septum IAS.

While various embodiments have been described above, it should be understood that they have been presented only as illustrations and examples of the present technology, and not by way of limitation. It will be apparent to persons skilled in the relevant art that various changes in form and detail may be made therein without departing from the spirit and scope of the present technology. Thus, the breadth and scope of the present technology should not be limited by any of the above-described embodiments, but should be defined only in accordance with the appended claims and their equivalents. It will also be understood that each feature of each embodiment discussed herein, and of each reference cited herein, may be used in combination with the features of any other embodiment. All patents and publications discussed herein are incorporated by reference herein in their entirety.

What is claimed is:

1. A method of delivering, positioning, and articulating a flanged device for percutaneously supporting and manipulating or articulating a septal wall of a heart, the method comprising the steps of:

advancing a distal anchor of a catheter-based system through a transseptal puncture in the septal wall of the heart, wherein the catheter-based system includes a catheter and a flanged device;

transitioning the distal anchor from a collapsed state to an expanded state;

retracting the catheter-based system such that a proximal surface of the distal anchor is adjacent to and engages with the septal wall within a first chamber of the heart and a proximal anchor of the flanged device is positioned within a second chamber of the heart;

transitioning the proximal anchor from a collapsed state to an expanded state, such that the flanged device is in an expanded configuration and is anchored to the septal wall;

advancing the catheter-based system such that the flanged device manipulates or articulates the septal wall to deform the septal wall;

advancing an auxiliary medical device through the catheter-based system to treat a native heart valve;

retracting the auxiliary medical device from the catheter-based system; and retracting the catheter-based system to permit the septal wall to return to a native shape or orientation.

2. The method of claim 1, wherein the distal anchor and the proximal anchor of the flanged device are each self-expanding.

3. The method of claim 1, wherein the distal anchor is a distal anchor balloon and the proximal anchor is a proximal anchor balloon, and the steps of transitioning the distal anchor from the collapsed state to the expanded state and the proximal anchor form the collapsed state to the expanded state includes inflating the distal anchor balloon from the collapsed state to the expanded state and inflating the proximal anchor balloon from the collapsed state to the expanded state.

4. The method of claim 1, wherein the flanged device is removably coupled to the catheter and further comprising the step of:

uncoupling the catheter from the flanged device.

5. The method of claim 1, wherein the catheter of the catheter-based system further includes an outer sheath, and the step of transitioning the distal anchor from the collapsed state to the expanded state includes first retracting the outer sheath of the catheter to release the distal anchor of the flanged device within the first chamber of the heart, and the step of transitioning the proximal anchor from the collapsed state to the expanded state includes first retracting the outer sheath of the catheter to release the proximal anchor of the flanged device within the second chamber of the heart.

6. The method of claim 1, further comprising the steps of:

transitioning the proximal anchor from the expanded state to the collapsed state; and transitioning the distal anchor from the expanded state to the collapsed state.

\* \* \* \* \*